Figure 5:
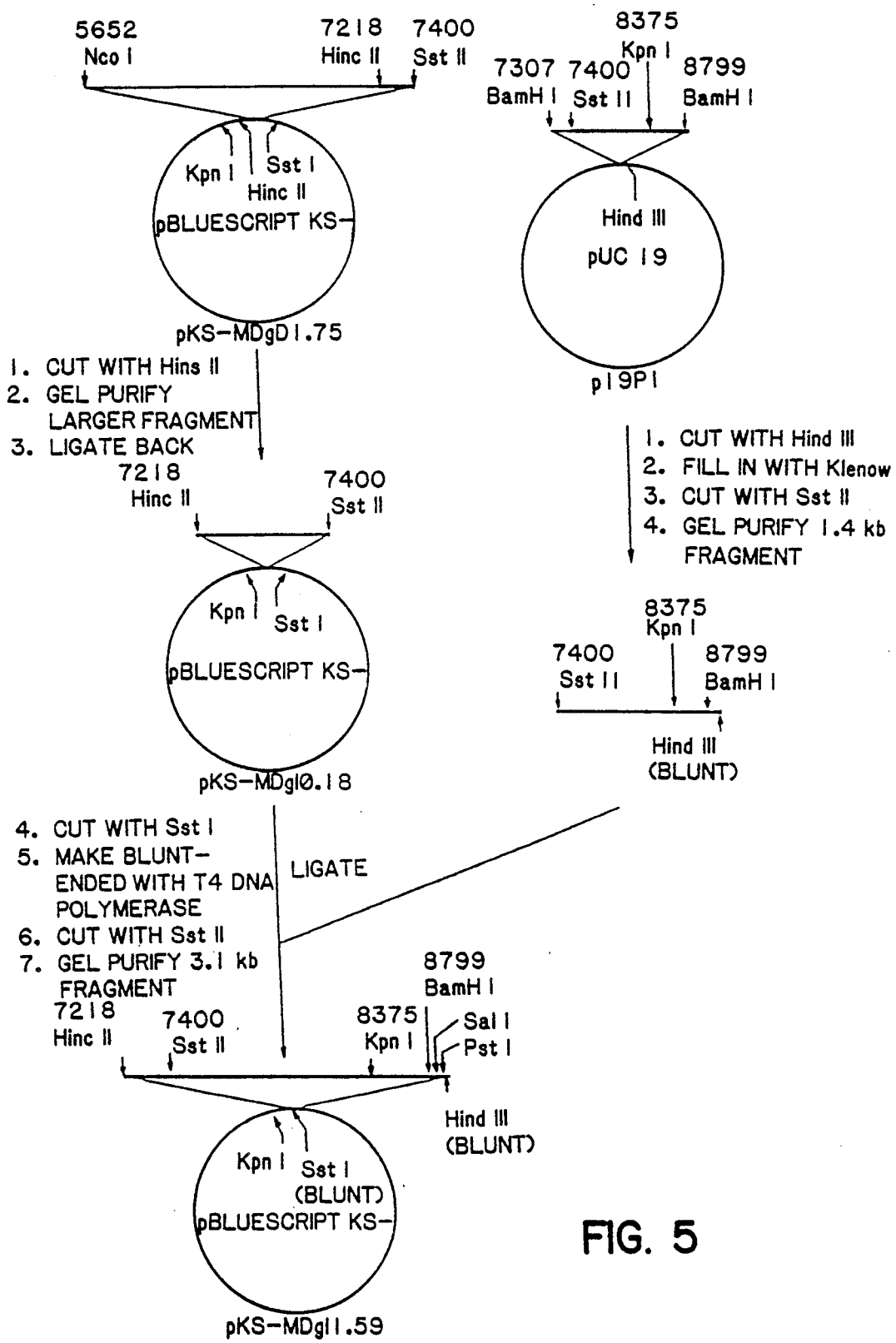

United States Patent [19]

Velicer et al.

[11] Patent Number: 5,138,033
[45] Date of Patent: Aug. 11, 1992

[54] MAREK'S DISEASE HERPESVIRUS GLYCOPROTEINS, GE

[75] Inventors: Leland F. Velicer; Peter Brunovskis, both of East Lansing; Paul M. Coussens, DeWitt, all of Mich.

[73] Assignee: Board of Trustees operating Michigan State University, East Lansing, Mich.

[21] Appl. No.: 572,711

[22] Filed: Aug. 24, 1990

[51] Int. Cl.⁵ ............................................. C07K 13/00
[52] U.S. Cl. .................................................... 530/395
[58] Field of Search ........................................ 530/395

[56] References Cited

PUBLICATIONS

Fukuchi et al, Journal of Virology, vol. 51, pp. 102–109, (1984).

Buckmaster et al., J. Gen. Virol., vol. 69, pp. 2033–2042, (1988).

*Primary Examiner*—Richard A. Schwartz
*Assistant Examiner*—S. C. Nolan
*Attorney, Agent, or Firm*—Ian C. McLeod

[57] ABSTRACT

DNA encoding glycopropteins gD, gI and part of gE from Marek's disease herpesvirus is described. The DNA is useful for probes to detect the DNA in the herpesvirus, for expression to produce the glycoproteins can be used for producing the antibodies which specifically recognize the three glycoprotein antigens, and in the case of the latter two genes, for potential insertion sites for foreign genes. Novel glycoproteins and regulatory sequences are also disclosed.

1 Claim, 13 Drawing Sheets

FIG. IA
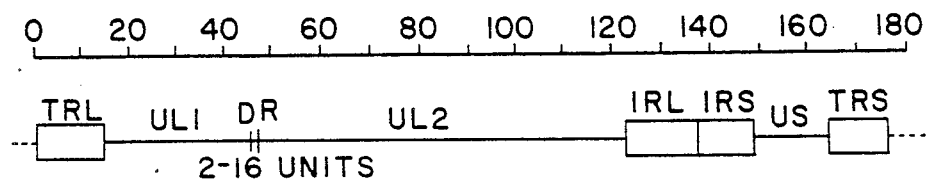
FIG. IB
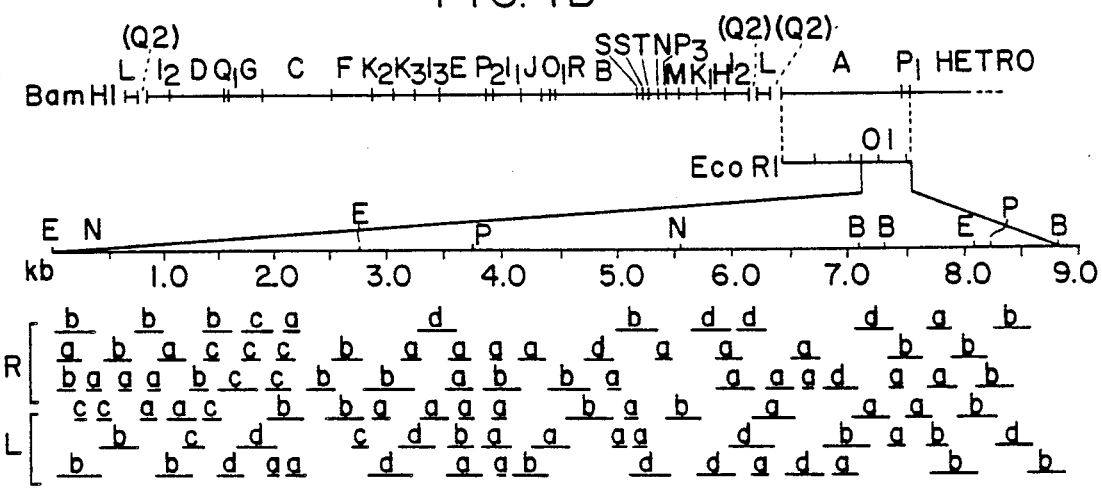
FIG. IC
US1  US10  SORF1  US2  US3  SORF2  US6  US7  US8

```
  1 GAATTCCTTGAAATTGGAGTGAAATCTTTAGGGAGGGAGGTTTACCATTGTGGAGAATAT
121 ACGTGATGTAAATTCTAGCAATTATTGTTCCTAGCAGAAGATAAAAGCTGGTAGCTATAT
    ATAGAGCAAGTAGTACATTAGGGGCTGGGTTAAAGACCAAGTAATTTTTGACCGGATATC  120
    AATACAGGCCAAAGTCTCCAAATTACACTTGAGCAGAAAACCTGCTTTCGGCTCCATCGG  240
```

US I
```
  1        M  S  R  D  R  D  R  A  R  P  D  T  R  L  S  S  S  D
241 AGGCAACATGAGTCGTGATCGAGATCGAGCCAGACCCGATACACGATTATCATCGTCAGA

N  E  S  D  D  E  D  Y  Q  L  P  H  S  H  P  E  Y  G  S  D    38
    TAATGAGAGCGACGACGAAGATTATCAACTGCCACATTCACATCCGGAATATGGCAGTGA  360

39 S  S  D  Q  D  F  E  L  N  N  V  G  K  F  C  P  L  P  W  K
361 CTCGTCCGATCAAGACTTTGAACTTAATAATGTGGGCAAATTTTGTCCTCTACCATGGAA

P  D  V  A  R  L  C  A  D  T  N  K  L  F  R  C  F  I  R  C    78
    ACCCGATGTCGCTCGGTTATGTGCGGATACAAACAAACTATTTCGATGTTTTATTCGATG  480

79 R  L  N  S  G  P  F  H  D  A  L  R  R  A  L  F  D  I  H  M
481 TCGACTAAATAGCGGTCCGTTCCACGATGCTCTTCGGAGAGCACTATTCGATATTCATAT

I  G  R  M  G  Y  R  L  K  Q  A  E  W  E  T  I  M  N  L  T   118
    GATTGGTCGAATGGGATATCGACTAAAACAAGCCGAATGGGAAACTATCATGAATTTGAC  600

119 P  R  Q  S  L  H  L  R  R  T  L  R  D  A  D  S  R  S  A  H
601 CCCACGCCAAAGTCTACATCTGCGCAGGACTCTGAGGGATGCTGATAGTCGAAGCGCCCA

P  I  S  D  I  Y  A  S  D  S  I  F  H  P  I  A  A  S  S  G  158
    TCCTATATCCGATATATATGCCTCCGATAGCATTTTTCACCCAATCGCTGCGTCCTCGGG  720

159 T  I  S  S  D  C  D  V  K  G  M  N  D  L  S  V  D  S  K  L
721 AACTATTTCTTCAGACTGCGATGTAAAAGGAATGAACGATTTGTCGGTAGACAGTAAATT
841 AGAGCCGACATTCTTTGATCTATCTAATGAGATAAAATAATAGATTTTGGATTTATTTGT

H  *                                                            179
    GCATTAACTATCCAGACTTGAAGAGAAAGCTCTTATTATATAATTTTAATTGTTAGACAT  840
    CATGATCTGTTGCAACAAACGCTGACCCCCCCCATCCATGAAGGGGCGTGTCAAATAACG  960
```

US I O
```
  1
961 TGTTGCCTTTTTGTTTGTATATGAAGATATTTAATGTGGCGTTGAGCCTAATGAGAGGAGA

M  A   2
    ACGTGTTTGAATACTGGAGACGAGCGCCGTGTAAGATTAAAACATATTGGAGAGGTATGG  1080

3    M  W  S  L  R  R  K  S  S  R  S  V  Q  L  R  V  D  S  P  K
1081 CCATGTGGTCTCTACGGCGCAAATCTAGCAGGAGTGTGCAACTCCGGGTAGATTCTCCAA

E  Q  S  Y  D  I  L  S  A  G  G  E  H  V  A  L  L  P  K  S   42
    AAGAACAGAGTTATGATATACTTTCTGCCGGCGGGGAACATGTTGCGCTATTGCCTAAAT  1200

43 V  R  S  L  A  R  T  I  L  T  A  A  T  I  S  Q  A  A  M  K
1201 CTGTACGCAGTCTAGCCAGGACCATATTAACCGCCGCTACGATCTCCCAGGCTGCTATGA

A  G  K  P  P  S  S  R  L  W  G  E  I  F  D  R  M  T  V  T   82
    AAGCTGGAAAACCACCATCGTCTCGTTTGTGGGGTGAGATATTCGACAGAATGACTGTCA  1320
```

FIG.2a

```
 83  L  N  E  Y  D  I  S  A  S  P  F  H  P  T  D  P  T  R  K  I
1321 CGCTTAACGAATATGATATTTCTGCTTCGCCATTCCACCCGACAGACCCGACGAGAAAAA

V  G  R  A  L  R  C  I  E  R  A  P  L  T  H  E  E  M  D  T  122
     TTGTAGGCCGGGCTTTACGGTGTATTGAACGTGCTCCTCTTACACACGAAGAAATGGACA 1440

123   R  F  T  I  M  M  Y  W  C  C  L  G  H  A  G  Y  C  T  V  S
1441 CTCGGTTTACTATCATGATGTATTGGTGTTGTCTTGGACATGCTGGATACTGTACTGTTT

R  L  Y  E  K  N  V  R  L  M  D  I  V  G  S  A  T  G  C  G  162
     CGCGCTTATATGAGAAGAATGTCCGTCTTATGGACATAGTAGGTTCGGCAACGGGCTGTG 1560

163    I  S  P  L  P  E  I  E  S  Y  W  K  P  L  C  R  A  V  A  T
1561 GAATAAGTCCACTCCCCGAAATAGAGTCTTATTGGAAACCTTTATGTCGTGCCGTCGCTA

K  G  N  A  A  I  G  D  D  A  E  L  A  H  Y  L  T  N  L  R  202
     CTAAGGGGAATGCAGCAATCGGTGATGATGCTGAATTGGCACATTATCTGACAAATCTTC 1680

203   E  S  P  T  G  D  G  E  S  Y  L  *
1681 GGGAATCGCCAACAGGAGACGGGGAATCCTACTTATAACTAATCGCACAATTATTAATAG
1801 CATTACAGTGTTGTCATGATTGTATGTATTATATGGGGTATGCATGAGGATTACTTCGAT
 351                       *  I  P  Y  A  H  P  N  S  R  N

213
     GATTTTAGGAAAAACTGCTACTAACGTTGTTTAAATAATAAAATTTTATTTTCAATAAGG 1800
     TGAAACTTTGTCTAAATGTCTGTAGGATTTTACTATTCATTAGTCTGGATCGAGGCGGAC 1920
     F  S  Q  R  F  T  Q  L  I  K  S  N  M  L  R  S  R  P  P  R  322

1921 GTAAATGGAGATTGCGGCAAATGTAGGGGTGCTGGTACATAAGACCTCCAACATCCATTC
 321  L  H  L  N  R  C  I  Y  P  H  Q  Y  M  L  G  G  V  D  M  R

GACTCATCGGCCTGCGTCCAAATGGATATGTTGATGTACCTTGTAAAGTTATGACATTAG 2040
      S  M  P  R  R  G  F  P  Y  T  S  T  G  Q  L  T  I  V  N  S   282

2041 AAGATCGATGGTGAATAGTGGGATCTATATCCATGCTATTCTCAATATTGCATGATATGC
 281  S  R  H  H  I  T  P  D  I  D  M  S  N  E  I  N  C  S  I  C

AATGTTCCCGGTTAGGTTTGATAAGATCATGTATGGTTCTATAATACAACTCCTCTTCAG 2160
      H  E  R  N  P  K  I  L  D  H  I  T  R  Y  Y  L  E  E  E  S   242

2161 AAGAATCATTTATTTTATGTCCACTGTCCTTGGATATTCCAGTTTCTGTCAATCGATTCG
 241  S  D  N  I  K  H  G  S  D  K  S  I  G  T  E  T  L  R  N  A

CTTGCATTTGCGTGCAGCATGTCTTGATGGCATTTCCTATGCTATCATCCGGCAGGCCTA 2280
      Q  M  Q  T  C  C  T  K  I  A  N  G  I  S  D  D  P  L  G  L  202

2281 AGGGTGTTCTATACTCGCACACAGGTAGAGCAAGAACCACGGCATATCGAGCTACCTCTA
 201  P  T  R  Y  E  C  V  P  L  A  L  V  V  A  Y  R  A  V  E  I

TTGCCCCGCTAAGGACATTTCTTGCAGACTGTATTGTCATGAACATATTTCGTGTATTGT 2400
      A  G  S  L  V  N  R  A  S  Q  I  T  M  F  M  N  R  T  N  H   162

2401 GTCGATCATAACCCTTGTTGATTCCTATGGAAAGCATTGTGGTCCAGTTTTCCAGATGAA
 161  R  D  Y  G  K  N  I  G  I  S  L  M  T  T  W  N  E  L  H  F
```

FIG.2b

```
              ATGAAAACAATGCGGGCAAAAATGGTCCCACCTGTTTCATCTTCAATGCATCTCTCACAT 2520
               S F L A P L F P G V Q K M K L A D R V D   122

2521 CCCAAGTTCTATAGAATATTCTCCACTGACCAGTTTCGGTAAGATCAGTTTCTGTAAAAT
          121 W T R Y F I R W Q G T E T L D T E T F N

TTGTGATAGTTTCAATCGAAAACATTTTGTCCATCATGGCAAAAAATCTATAGGCAGACC 2640
               T I T E I S F M K D M M A F F R Y A S W    82

2641 AGATAACCATTTGACACCACATATCCTTGTGTATATCAAACGATGTAATAGATCCCTCGT
           81 I V M Q C W M D K H I D F S T I S G E N

TAGTAGATATGGTACATAAAAGGCCTAATCTCTCTCGGGCTTCCATACATTGAACGATTC 2760
               T S I T C L L G L R E R A E M C Q V I G   42

2761 CTTCTGTGAATTCATCAACAACCACATGCCAAAAATTTACATTAGTAATCTTTCTCGGTG
           41 E T F E D V V V H W F N V N T I K R P P

GCTTACCAAATCGTCCTCTTGGTATATCCATATCATCGAACATTGTAGCATTGACTCTGC 2880
               K G F R G R P I D M D D F M T A N V R S    2

SORF1   2881 TCATCGTTGTCTTTCAAATGCGCTCGATTGTTGAATCTCTCCTGATGTTAGAAGTATATG
            1 M

GAAGATAGCCTGGATACATAAGTGATCTAGAAGGGTTTGTTATTGCACTAAATATACAAAT 3000
                                                                             1

3001 TATACGTGACACTATAGCGACGGTTGTAGCGATGCACCTAATCGTAATGTGTATACGCCC
          270

CATCATGTAATTATATCTAATTGGTAGCAAGTAGGTCTGTCGAATAACAGCTAATGACTA 3120
                      *                                         H S G 268

3121 CCGGCTCTACATTTTTTCTGTATTCGTGACTTTCCTGTCGCAGTGTAAGGAACCGGAATT
          267 A R C K K Q I R S K G T A T Y R V P I A

GCAATCGCATCTCTATCTTCTTTCTTGCAACATTTTCCACAACAGAATAATCTGCCGGGT 3240
               I A D R D E K K C C K G C C F L R G P T   228

3241 GTACTACTCATTTGAGGTGGTTCGATTTCCGGAGGTTTTAGAGGATTGGGTGGGGACCCG
          227 S S M Q P P E I E P P K L P N P P S G L

AGGATTTTGTATACACATACCATATCACTGTCGCAAAAATGCGCTCTATCTTCTGGGGTG 3360
               I K Y V C V M D S D C F H A R D E P T D   188

3361 TCGAACTTCGGTTCCCATGTAGATGTCAAGAGAGTTTGAATATTGTCGGGAATGGCCCAC
          187 F K P E W T S T L L I G I N D P I A W P

GGCATACCGGACCAGGTCCCAGACACTTTGATTGCAAGTAACCTTTTTGGCAAAGGAATA 3480
               M G S W T G S V K I A L L R K P L P I C   148

3481 CATTCGAGCGCAATGGCACATATATCTGCCGCCCCAACTATCCACAAGCTATGTGGAGCA
          147 E L A I A C I D A A G V I W L S H P A N
```

FIG. 2c

```
       TTACCAGAAACTTCAGATTCCAACATCAAATATCCAGATAGAACATCCTGCCATTCTGTG 3600
        G  S  V  E  S  E  L  M  L  Y  G  S  L  V  D  Q  W  E  T  S   108

3601 GAACATCCTGCAACATCTTCAAATAGCCGCACTATAAACGAATCCCTAGTTCCGGCCAAT
    107  C  G  A  V  D  E  F  L  R  V  I  F  S  D  R  T  G  A  L  G

CCGGTACCACGAACTCCAGTTCCATCTGGTGGCTTTGTCCTTACTATCGGTCGATGTTGC 3720
         T  G  R  V  G  T  G  D  P  P  K  T  R  V  I  P  R  H  Q  R   68

3721 CGAGGAAGAATTAACATGGGTTTGGCAAAACGGAATAGGTCTGCAGCTCTGGCGATTATG
    67   P  L  I  L  M  P  K  A  F  R  F  L  D  A  A  R  A  I  I  P

GGCACACCCACATCATCCTGTATTTGTTCCATACATTGCTTTATAAGGAATATCCATAAA 3840
         V  G  V  D  D  Q  I  Q  E  M  C  Q  K  I  L  F  I  W  L  T   28

3841 GTAGATGCAGCATCTCTAGATCTTCCTGGCAATCGATCGCATTCATCTAGAAGTGTGACT
US2  27   S  A  A  D  R  S  R  G -P  L  R  D  C  E  D  L  L  T  V  I

ATAGTTATCATGGACACACCCATCTTCACCTCCACCAATAATCTTTTTTATTGTTAATAA 3960
          T  I  M  S  V  G  M
US3    1                                                                  1
   3961 CTGGGCCGGTCTGATCTCCAAATCTTATACTCTGGTAGAATATGAAACAGGGTTAAAACT
                                                 M  E  C  G  I  S  S   7
        AGGTAATAGACTGGAGTTCTTCGACTCCGGAGGCAGAAACGATGGAATGTGGCATTTCTT 4080
      8   S  K  V  H  D  S  K  T  N  T  T  Y  G  I  I  H  N  S  I  N
   4081 CGTCGAAAGTACACGACTCTAAAACTAATACTACCTACGGAATTATACATAACAGCATCA

G  T  D  T  T  L  F  D  T  F  P  D  S  T  D  N  A  E  V  T   47
        ATGGTACGGATACGACGTTGTTTGATACTTTTCCGACAGTACCGATAACGCGGAAGTGA  4200

48  G  D  V  D  D  V  K  T  E  S  S  P  E  S  Q  S  E  D  L  S
   4201 CGGGGGATGTGGACGATGTGAAGACTGAGAGCTCTCCCGAGTCCCAATCTGAAGATTTGT

P  F  G  N  D  G  N  E  S  P  E  T  V  T  D  I  D  A  V  S   87
        CACCTTTTGGGAACGATGGAAATGAATCCCCCGAAACGGTGACGGACATTGATGCAGTTT 4320

88  A  V  R  M  Q  Y  N  I  V  S  S  L  P  P  G  S  E  G  Y  I
   4321 CAGCTGTGCGAATGCAGTATAACATTGTTTCATCGTTACCGCCCGGATCTGAAGGGTATA

Y  V  C  T  K  R  G  D  N  T  K  R  K  V  I  V  K  A  V  T   127
        TCTATGTTTGTACAAAGCGTGGGGATAATACCAAGAGAAAAGTCATTGTGAAAGCTGTGA 4440

128  G  G  K  T  L  G  S  E  I  D  I  L  K  K  M  S  H  R  S  I
   4441 CTGGTGGCAAAACCCTTGGGAGTGAAATTGATATATTAAAAAAAATGTCTCACCGCTCCA

I  R  L  V  H  A  Y  R  W  K  S  T  V  C  M  V  M  P  K  Y   167
        TAATTAGATTAGTTCATGCTTATAGATGGAAATCGACAGTTTGTATGGTAATGCCTAAAT 4560

168  K  C  D  L  F  T  Y  I  D  I  M  G  P  L  P  L  N  Q  I  I
   4561 ACAAATGCGACTTGTTTACGTACATAGATATCATGGGACCATTGCCACTAAATCAAATAA

T  I  E  R  G  L  L  G  A  L  A  Y  I  H  E  K  G  I  I  H   207
        TTACGATAGAACGGGGTTTGCTTGGAGCATTGGCATATATCCACGAAAAGGGTATAATAC 4680
```

FIG.2d

```
     208  R  D  V  K  T  E  N  I  F  L  D  K  P  E  N  V  V  L  G  D
    4681 ATCGTGATGTAAAAACTGAAAATATATTTTTGGATAAACCTGAAAATGTAGTATTGGGGG

F  G  A  A  C  K  L  D  E  H  T  D  K  P  K  C  Y  G  W  S  247
         ACTTTGGGGCAGCATGTAAATTAGATGAACATACAGATAAACCCAAATGTTATGGATGGA 4800

248  G  T  L  E  T  N  S  P  E  L  L  A  L  D  P  Y  C  T  K  T
    4801 GTGGAACTCTGGAAACCAATTCGCCTGAACTGCTTGCACTTGATCCATACTGTACAAAAA

D  I  W  S  A  G  L  V  L  F  E  M  S  V  K  N  I  T  F  F  287
          CTGATATATGGAGTGCAGGATTAGTTCTGTTTGAGATGTCAGTAAAAAATATAACCTTTT 4920

288  G  K  Q  V  N  G  S  G  S  Q  L  R  S  I  I  R  C  L  Q  V
    4921 TTGGCAAACAAGTAAACGGCTCAGGTTCTCAGCTGAGATCCATAATTAGATGCCTGCAAG

H  P  L  E  F  P  Q  N  N  S  T  N  L  C  K  H  F  K  Q  Y  327
         TCCATCCGTTGGAATTTCCACAGAACAATTCTACAAACTTATGCAAACACTTCAAGCAGT 5040

328  A  I  Q  L  R  H  P  Y  A  I  P  Q  I  I  R  K  S  G  M  T
    5041 ACGCGATTCAGTTACGACATCCATATGCAATCCCTCAGATTATACGAAAGAGTGGTATGA

M  D  L  E  Y  A  I  A  K  M  L  T  F  D  Q  E  F  R  P  S  367
         CGATGGATCTTGAATATGCTATTGCAAAAATGCTCACATTCGATCAGGAGTTTAGACCAT 5160

368  A  Q  D  I  L  M  L  P  L  F  T  K  E  P  A  D  A  L  Y  T
    5161 CTGCCCAAGATATTTTAATGTTGCCTCTTTTTACTAAAGAACCCGCTGACGCATTATACA

I  T  A  A  H  M  *                                         393
          CGATAACTGCCGCTCATATGTAAACACCCGTCAAAAATAACTTCAATGATTCATTTTATA 5280

SORF2  1
    5281 ATATATACTACGCGTTACCTGCAATAATGACAACATTCGAAGTCTTTGAAGATTCGCAGA

M  A  P  S  G  P  T  P  Y  S  H  R  P  Q  I  K  16
         CCTTTTTTGCGAATGGCACCTTCGGGACCTACGCCATATTCCCACAGACCGCAAATAAAG 5400

17  H  Y  G  T  F  S  D  C  M  R  Y  T  L  N  D  V  C  K  V  D
    5401 CATTATGGAACATTTTCGGATTGCATGAGATATACTCTAAACGATGTGTGTAAGGTAGAT

D  R  C  S  D  I  H  N  S  L  A  Q  S  N  V  T  S  S  M  S  56
         GATAGATGTTCAGACATACATAACTCCTTAGCACAATCCAATGTTACTTCAAGCATGTCT 5520

57  V  M  N  D  S  E  E  C  P  L  I  N  G  P  S  M  Q  A  E  D
    5521 GTAATGAACGATTCGGAAGAATGTCCATTAATAAATGGACCTTCGATGCAGGCAGAGGAC

P  K  S  V  F  Y  K  V  R  K  P  D  R  S  R  D  F  S  W  Q  96
         CCTAAAAAGTGTTTTTTATAAAGTTCGTAAGCCTGACCGAAGTCGTCATTTTTCATGGCAA 5640

97  N  L  N  S  H  G  N  S  G  L  R  R  E  K  Y  I  R  S  S  K
    5641 AATCTGAACTCCCATGGCAATAGTGGTCTACGTCGTGAAAAATATATACGTTCCTCTAAG

R  R  W  K  N  P  E  I  F  K  V  S  L  K  C  E  S  I  G  A  136
         AGGCGATGGAAGAATCCCGAGATATTTAAGGTATCTTTGAAATGTGAATCAATTGGCGCT 5760
```

FIG.2e

```
                137  G  N  G  I  K  I  S  F  S  F  F   *
               5761  GGTAACGGAATAAAAATTTCATTCTCATTTTTCTAACATTATAATATATCAGATCGTTTC

147
                    TTATATACTTATTTTTCATCGTCGGGATATGACTAACGTATACTAAGTTACAAGAAACAAC 5880
     US6      1
     (gD) 5881 TGCTTAACGTCGAACATAACGGAAATAAAAATATATATAGCGTCTCCTATAACTGTTATA

M  N  R  Y  R  Y  E  S  I  F  F  R  Y   13
                    TTGGCACCTTTTAGAGCTTCGGTATGAATAGATACAGATATGAAAGTATTTTTTTTAGAT 6000

14  I  S  S  T  R  M  I  L  I  I  C  L  L  L  G  T  G  D  M  S
               6001 ATATCTCATCCACGAGAATGATTCTTATAATCTGTTTACTTTTGGGAACTGGGGACATGT

A  M  G  L  K  K  D  N  S  P  I  I  P  T  L  H  P  K  G  N   53
                    CCGCAATGGGACTTAAGAAAGACAATTCTCCGATCATTCCCACATTACATCCGAAAGGTA 6120

54  E  N  L  R  A  T  L  N  E  Y  K  I  P  S  P  L  F  D  T  L
               6121 ATGAAAACCTCCGGGCTACTCTCAATGAATACAAAATCCCGTCTCCACTGTTTGATACAC

D  N  S  Y  E  T  K  H  V  I  Y  T  D  N  C  S  F  A  V  L   93
                    TTGACAATTCATATGAGACAAAACACGTAATATATACGGATAATTGTAGTTTTGCTGTTT 6240

94  N  P  F  G  D  P  K  Y  T  L  L  S  L  L  L  M  G  R  R  K
               6241 TGAATCCATTTGGCGATCCGAAATATACGCTTCTCAGTTTACTGTTGATGGGACGACGCA

Y  D  A  L  V  A  W  F  V  L  G  R  A  C  G  R  P  I  Y  L   133
                    AATATGATGCTCTAGTAGCATGGTTTGTCTTGGGCAGAGCATGTGGGAGACCAATTTATT 6360

134  R  E  Y  A  N  C  S  T  N  E  P  F  G  T  C  K  L  K  S  L
               6361 TACGTGAATATGCCAACTGCTCTACTAATGAACCATTTGGAACTTGTAAATTAAAGTCCC

G  W  W  D  R  R  Y  A  M  T  S  Y  I  D  R  D  E  L  K  L   173
                    TAGGATGGTGGGATAGAAGATATGCAATGACGAGTTATATCGATCGAGATGAATTGAAAT 6480

174  I  I  A  A  P  S  R  E  L  S  G  L  Y  T  R  L  I  I  I  N
               6481 TGATTATTGCAGCACCCAGTCGTGAGCTAAGTGGATTATATACGCGTTTAATAATTATTA

G  E  P  I  S  S  D  I  L  L  T  V  K  G  T  C  S  F  S  R   213
                    ATGGAGAACCCATTTCGAGTGACATATTACTGACTGTTAAAGGAACATGTAGTTTTTCGA 6600

214  R  G  I  K  D  N  K  L  C  K  P  F  S  F  F  V  N  G  T  T
               6601 GACGGGGGATAAAGGATAACAAACTATGCAAACCGTTCAGTTTTTTTGTCAATGGTACAA

R  L  L  D  M  V  R  T  G  T  P  R  A  H  E  E  N  V  K  Q   253
                    CACGGCTGTTAGACATGGTGCGAACAGGAACCCCGAGAGCCCATGAAGAAAATGTGAAGC 6720

254  W  L  E  R  N  G  G  K  H  L  P  I  V  V  E  T  S  M  Q  Q
               6721 AGTGGCTTGAACGAAATGGTGGTAAACATCTACCAATCGTCGTCGAAACATCTATGCAAC

V  S  N  L  P  R  S  F  R  D  S  Y  L  K  S  P  D  D  D  K   293
                    AAGTCTCAAATTTGCCGAGAAGTTTTAGAGATTCATATTTAAAATCACCTGACGACGATA 6840
```

FIG.2f

```
      294  Y  N  D  V  K  M  T  S  A  T  T  N  N  I  T  T  S  V  D  G
     6841  AATATAATGACGTCAAAATGACATCGGCCACTACTAATAACATTACCACCTCCGTGGATG

Y  T  G  L  T  N  R  P  E  D  F  E  K  A  P  Y  I  T  K  R   333
           GTTACACTGGACTCACTAATCGGCCCGAGGACTTTGAGAAAGCACCATACATAACTAAAC  6960

334  P  I  I  S  V  E  E  A  S  S  Q  S  P  K  I  S  T  E  K  K
     6961  GACCGATAATCTCTGTCGAGGAGGCATCCAGTCAATCACCTAAAATATCAACAGAAAAAA

S  R  T  Q  I  I  I  S  L  V  V  L  C  V  M  F  C  F  I  V   373
              AATCCCGAACGCAAATAATAATTTCACTAGTTGTTCTATGCGTCATGTTTTGTTTCATTG  7080

374  I  G  S  G  I  W  I  L  R  K  H  R  K  T  V  M  Y  D  R  R
     7081  TAATCGGGTCTGGTATATGGATCCTTCGCAAACACCGCAAAACGGTGATGTATGATAGAC

R  P  S  R  R  A  Y  S  R  L  *                              403
                 GTCGTCCATCAAGACGGGCATATTCCCGCCTATAACACGTGTTTGGTATGGGCGTGTCGC  7200

US7      1
(gI)  7201  TATAGTGCATAAGAAGTTGACTACATTGATCAATGACATTATATAGCTTCTTTGGTCAGA

M  Y  V  L  Q  L  L  F  W  I  R  L  F   13
           TAGACGGCGTGTGTGATTGCGATGTATGTACTACAATTATTATTTTGGATCCGCCTCTTT  7320

14  R  G  I  W  S  I  V  Y  T  G  T  S  V  T  L  S  T  D  Q  S
     7321  CGAGGCATCTGGTCTATAGTTTATACTGGAACATCTGTTACGTTATCAACGGACCAATCT

A  L  V  A  F  R  G  L  D  K  M  V  N  V  R  G  Q  L  L  F   53
              GCTCTTGTTGCGTTCCGCGGATTAGATAAAATGGTGAATGTACGCGGCCAACTTTTATTC  7440

54  L  G  D  Q  T  R  T  S  S  Y  T  G  T  T  E  I  L  K  W  D
     7441  CTGGGCGACCAGACTCGGACCAGTTCTTATACAGGAACGACGGAAATCTTGAAATGGGAT

E  E  Y  K  C  Y  S  V  L  H  A  T  S  Y  M  D  C  P  A  I   93
                    GAAGAATATAAATGCTATTCCGTTCTACATGCGACATCATATATGGATTGTCCTGCTATA  7560

94  D  A  T  V  F  R  G  C  R  D  A  V  V  Y  A  Q  P  H  G  R
     7561  GACGCCACGGTATTCAGAGGCTGTAGAGACGCTGTGGTATATGCTCAACCTCATGGTAGA

V  Q  P  F  P  E  K  G  T  L  L  R  I  V  E  P  R  V  S  D   133
                 GTACAACCTTTTCCCGAAAAGGGAACATTGTTGAGAATTGTCGAACCCAGAGTATCAGAT  7680

134  T  G  S  Y  Y  I  R  V  S  L  A  G  R  N  M  S  D  I  F  R
     7681  ACAGGCAGCTATTACATACGTGTATCTCTCGCTGGAAGAAATATGAGCGATATATTTAGA

M  V  V  I  I  R  S  S  K  S  W  A  C  N  H  S  A  S  S  F   173
           ATGGTTGTTATTATAAGGAGTAGCAAATCTTGGGCCTGTAATCACTCTGCTAGTTCATTT  7800

174  Q  A  H  K  C  I  R  Y  V  D  R  M  A  F  E  N  Y  L  I  G
     7801  CAGGCCCATAAATGTATTCGCTATGTCGACCGTATGGCCTTTGAAAATTATCTGATTGGA

H  V  G  N  L  L  D  S  D  S  E  L  H  A  I  Y  N  I  T  P   213
              CATGTAGGCAATTTGCTGGACAGTGACTCGGAATTGCATGCAATTTATAATATTACTCCC  7920
```

FIG.2g

```
    214 Q  S  I  S  T  D  I  N  I  V  T  T  P  F  Y  D  N  S  G  T
   7921 CAATCCATTTCCACAGATATTAATATTGTAACGACTCCATTTTACGATAATTCGGGAACA

I  Y  S  P  T  V  F  N  L  F  N  N  N  S  H  V  D  A  M  N    253
        ATTTATTCACCTACGGTTTTTAATTTGTTTAATAACAATTCCCATGTCGATGCAATGAAT  8040

254 S  T  G  M  W  N  T  V  L  K  Y  T  L  P  R  L  I  Y  F  S
   8041 TCGACTGGTATGTGGAATACCGTTTTAAAATATACCCTTCCAAGGCTTATTTACTTTTCT

T  M  I  V  L  C  I  I  A  L  A  I  Y  L  V  C  E  R  C  R    293
        ACGATGATTGTACTATGTATAATAGCATTGGCAATTTATTTGGTCTGTGAAAGGTGCCGC  8160

294 S  P  H  R  R  I  Y  I  G  E  P  R  S  D  E  A  P  L  I  T
   8161 TCTCCCCATCGTAGGATATACATCGGTGAACCAAGATCTGATGAGGCCCCACTCATCACT

S  A  V  N  E  S  F  Q  Y  D  Y  N  V  K  E  T  P  S  D  V    333
        TCTGCAGTTAACGAATCATTTCAATATGATTATAATGTAAAGGAAACTCCTTCAGATGTT  8280

334 I  E  K  E  L  M  E  K  L  K  K  K  V  E  L  L  E  R  E  E
   8281 ATTGAAAAGGAGTTGATGGAAAAACTGAAGAAGAAAGTCGAATTGTTGGAAAGAGAAGAA

C  V  *                                                         355
        TGTGTATAGGTTTGAGAAACTATTATAGGTAGGTGGTACCTGTTAGCTTAGTATAAGGGG  8400

US8    1
(gE) 8401 AGGAGCCGTTTCTTGTTTTAAAGACACGAACACAAGGCCGTAAGTTTTATATGTGAATTT

M  C  V  F  Q  I  L  L  I  V  T    11
        TGTGCATGTCTGCGAGTCAGCGTCATAATGTGTGTTTTCCAAATCCTGATAATAGTGACG  8520

12 T  I  K  V  A  G  T  A  N  I  N  H  I  D  V  P  R  G  H  S
   8521 ACGATCAAAGTAGCTGGAACGGCCAACATAAATCATATAGACGTTCCTCGAGGACATTCT

A  T  T  I  P  R  Y  P  P  V  V  D  G  T  L  Y  T  E  T       51
        GCTACAACGACGATCCCGCGATATCCACCAGTTGTCGATGGGACCCTTTACACCGAGACG  8640

52 W  T  W  I  P  N  H  C  N  E  T  A  T  G  Y  V  C  L  E  S
   8641 TGGACATGGATTCCCAATCACTGCAACGAAACGGCAACAGGCTATGTATGTCTGGAAAGT

A  H  C  F  T  D  L  I  L  G  V  S  C  M  R  Y  A  D  E  I    91
        GCTCACTGTTTTACCGATTTGATATTAGGAGTATCCTGCATGAGGTATGCGGATGAAATC  8760

92 V  L  R  T  D  K  F  I  V  D  A  G  S     104
   8761 GTCTTACGAACTGATAAATTTATTGTCGATGCGGGATCC  8799
```

FIG. 2h

FIG.3A

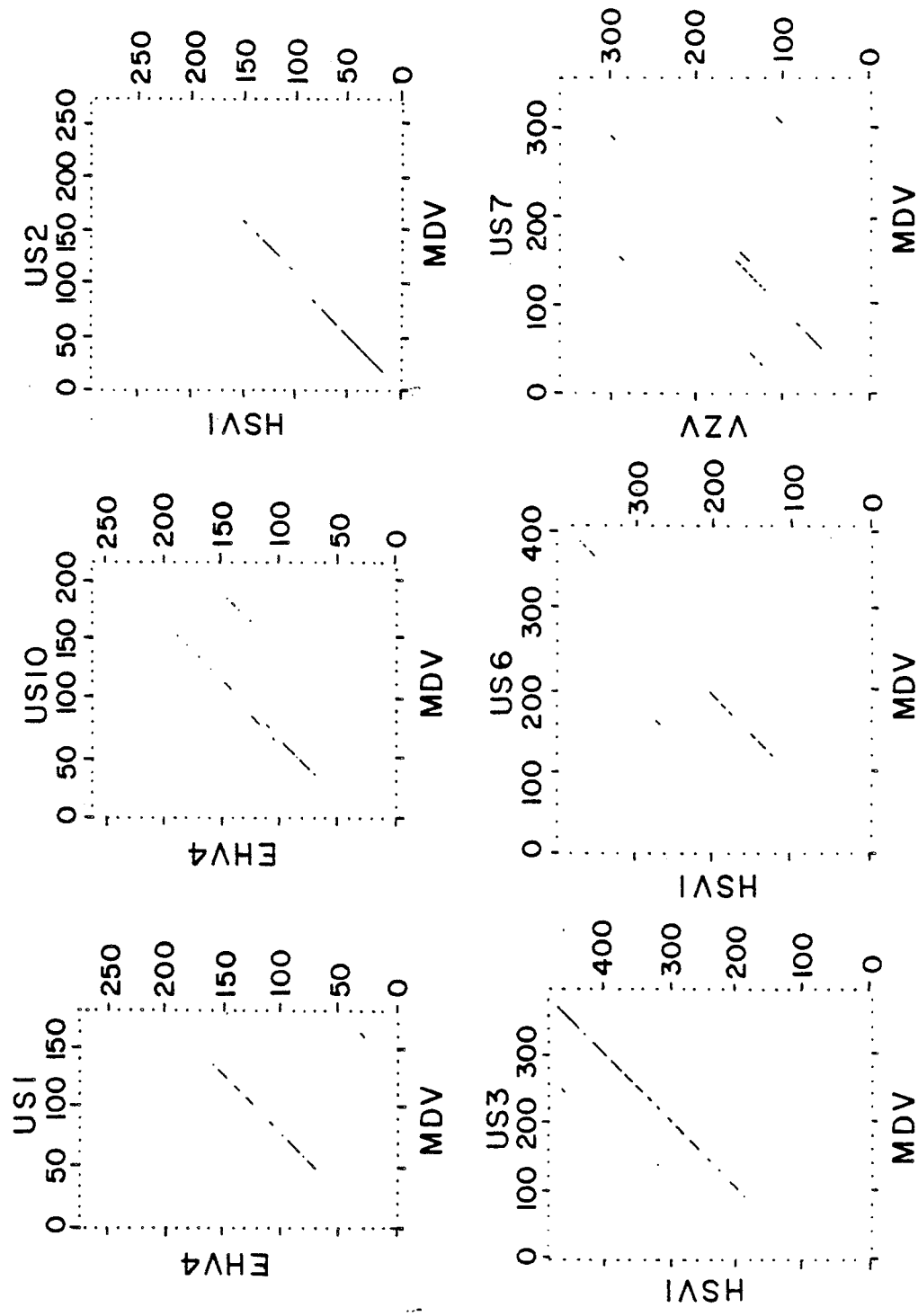

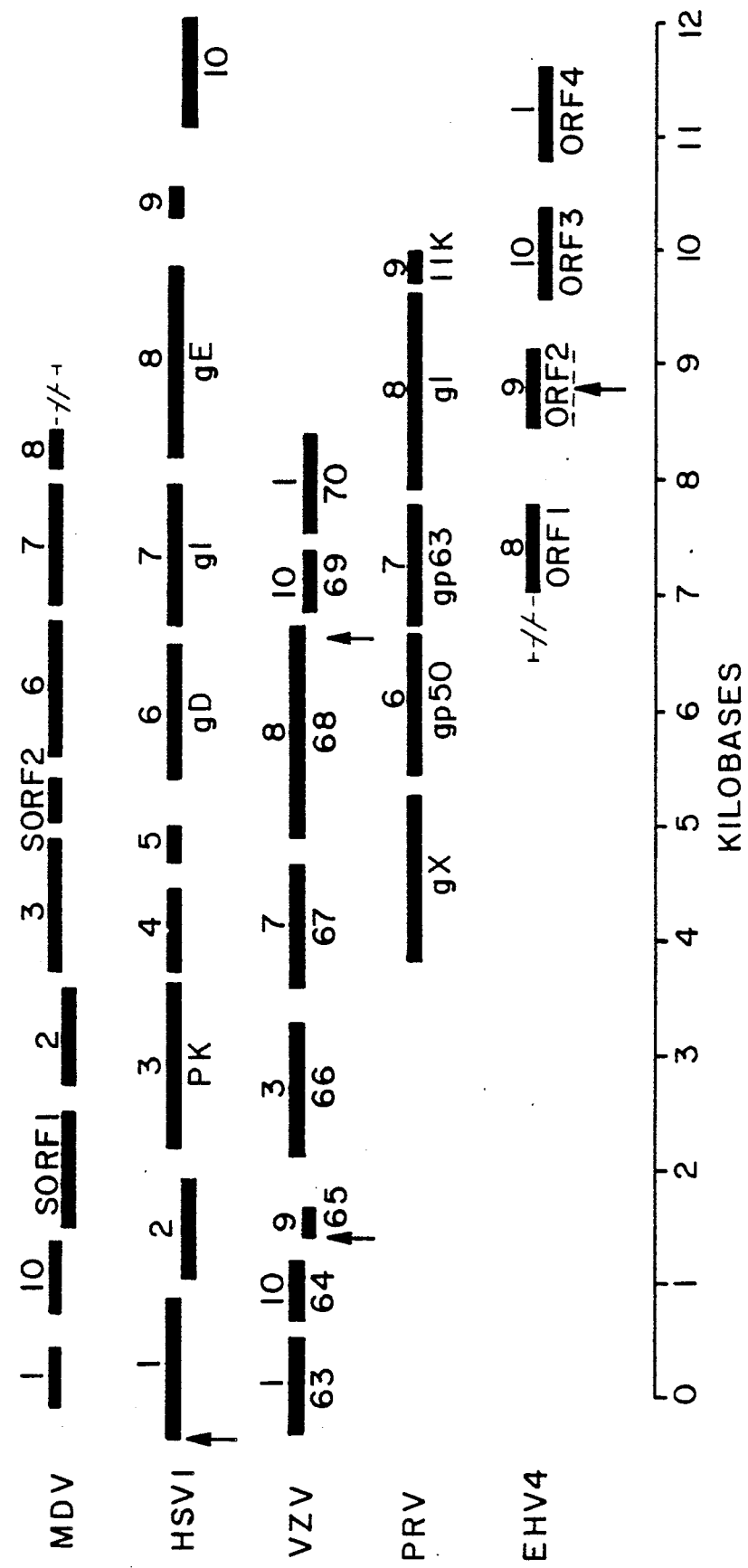

MAREK'S DISEASE HERPESVIRUS GLYCOPROTEINS, GE

BACKGROUND OF THE INVENTION (1) Field of the Invention

The present invention relates to segments of the Marek's Disease Herpesvirus genome, from its unique short ($U_s$) region encoding glycoproteins gD, gI and part of gE, and to novel glycoproteins produced therefrom. In particular, the present invention relates to DNA segments encoding these glycoprotein antigens and the 5' regulatory region of their genes, segments which are useful for probing for Marek's disease herpesvirus, as a possible source for MDV promoters, for gene expression to produce the glycoproteins that in turn can be used for producing antibodies which recognize the three glycoprotein antigens, and in the case of the latter two genes, for potential insertion sites for foreign genes.

(2) Prior Art

Marek's disease virus (MDV) is an oncogenic herpesvirus of chickens, which is known to cause T cell lymphomas and peripheral nerve demyelination. The resulting disease, Marek's disease (MD), was the first naturally occurring lymphomatous disorder to be effectively controlled via vaccination with the antigenically related, yet apathogenic herpesvirus of turkeys (HVT).

Because of similar biological properties, especially its lymphotropism, MDV has been classified as a member of the gammaherpesvirus subfamily (Roizman, B., et al., Intervirology 16:201-217 (1981)). Of the three herpesvirus subfamilies, gammaherpesviruses exhibit particularly marked differences with regard to genome composition and organization. For example, the B-lymphotropic Epstein-Barr virus (EBV) of humans has a 172.3 kbp genome with 60% G+C content, is bounded by terminal 0.5 kbp direct repeats and contains a characteristic set of internal 3.07 kbp tandem repeats (Baer, R., et al., Nature (London) 310:207-211 (1984)). Herpesvirus saimiri (HVS), a T-lymphotropic herpesvirus of newworld monkeys and lower vertebrates, has an A+T rich coding sequence (112 kbp; 36% G+C; i.e. L-DNA) without any large-scale internal redundancy, but contains instead greater than 30 reiterations of a 1.44 kbp sequence of 71% G+C at the termini of the genome (H-DNA) (Banker, A. T., et al., J. Virol. 55:133-139 (1985)). Despite the structural differences between EBV and HVS, the genomes of these two viruses encode serologically related proteins and share a common organization of coding sequences which differs from that of the neurotropic alphaherpesviruses, exemplified by herpes simplex virus (HSV) and varicella-zoster virus (VZV) (Camerion, K. R., et al., J. Virol. 61:2063-2070 (1987); Davison, A. J., et al., J. Gen. Virol. 68:1067-1079 (1987); Davison, A. J., et al., J. Gen. Virol. 67:597-611 (1986; Davison, A. J., et al., J. Gen. Virol. 76:1759-1816 (1986); Davison, A. J., et al., J. Gen. Virol. 64:1927-1942 (1983); Gompels, U. A., J. of Virol. 62:757-767 (1988); and Nichols, J., et al., J. of Virol. 62:3250-3257 (1988)).

In contrast to other gammaherpesviruses, MDV has a genome structure closely resembling that of the alphaherpesviruses (Cebrian, J., et al., Proc. Natl. Acad. Sci. USA 79:555-558 (1982); and Fukuchi, K., et al., J. Virol. 51:102-109 (1984)). Members of the latter subfamily have similar genome structures consisting of covalently joined long (L) and short (S) segments. Each segment comprises a unique (U) segment ($U_L$, $U_S$) flanked by a pair (terminal and internals) of inverted repeat regions ($TR_L$, $IR_L$; $TR_S$, $IR_S$, respectively). Alphaherpesviruses include human HSV and VZV, porcine pseudorabies virus (PRV), bovine herpesvirus (BHV) and equine herpesvirus (EHV). Because MDV contains extensive repeat sequences flanking its $U_L$ region, its genome structure most resembles that of HSV (Cebrian, J., et al., Proc. Natl. Acad. Sci. USA 79:555-558 (1982); and Fukuchi, K., et al., J. Virol. 51:102-109 (1984)).

Recent studies (Buckmaster, A. E., et al., J. Gen. Virol. 69:2033-2042 (1988)) have shown that the two gammaherpesviruses, MDV and HVT, appear to bear greater similarity to the alphaherpesviruses, VZV and HSV, than to the gammaherpesvirus, EBV. This was based on a comparison of numerous randomly isolated MDV and HVT clones at the predicted amino acid level; not only did individual sequences exhibit greater relatedness to alphaherpesvirus genes than to gammaherpesvirus genes, but the two viral genomes were found to be generally collinear with VZV, at least with respect to the unique long ($U_L$) region. Such collinearity of $U_L$ genes extends to other alphaherpesviruses such as HSV-1, HSV-2, EHV-1 and PRV as evidenced by both sequence analysis (McGeoch, D. J., et al., J. Gen. Virol. 69:1531-1574 (1988)) and DNA hybridization experiments (Davison, A. J., et al., J. Gen. Virol. 64:1927-1942 (1983)). Many of these $U_L$ genes are shared by other herpesviruses, including the beta- and gammaherpesviruses (Davison, A. J., et al., J. Gen. Virol. 68:1067-1079 (1987)). The organization and comparison of such genes has suggested the past occurrence of large-scale rearrangements to account for the divergence of herpesviruses from a common ancestor. Unfortunately, such a hypothesis fails to account for the presence of alphaherpesvirus s component (unique short, $U_S$, and associated inverted/terminal repeat short, $IR_S$, $TR_S$) genes which appear unique to members of this subfamily (Davison, A. J., et al., J. Gen. Virol. 68:1067-1079 (1987); Davison, A. J., et al., J. Gen. Virol. 67:597-611 (1986; and McGeoch, D. J., et al., J. Mol. Biol. 181:1-13. (1985)).

In addition to its uniqueness compared with beta- and gammaherpesviruses, the alphaherpesvirus $U_S$ region is particularly interesting because of marked differences in its content and genetic organization within the latter subfamily (e.g. HSV-1 US=13.0 kbp, 12 genes, McGeoch, D. J., et al., J. Mol. Biol. 181:1-13. (1985); VZV US=5.2 kbp, 4 genes, Davison, A. J., et al., J. Gen. Virol. 76:1759-1816 (1986)). In the case of HSV-1, 11 of the 12 US genes have been found to be dispensable for replication in cell culture (Longnecker, R., et al., Proc. Natl. Acad. Sci. USA 84:4303-4307 (1987)). This has suggested the potential involvement of these genes in pathogenesis and/or latency (Longnecker, R., et al., Proc. Natl. Acad. Sci. USA 84:4303-4307 (1987); Meignier, B., et al., Virology 162:251-254 (1988); and Weber, P. C., et al., Science 236:576-579 (1987)). In the report by Buckmaster et al. (Buckmaster, A. E., et al., J. Gen. Virol. 69:2033-2042 (1988)), except for the identification of partial MDV sequences homologous to HSV immediate early protein α22 (US1) and the serine-threonine protein kinase (US3), the content, localization and organization of MDV S component homologs was not determined. Moreover, despite the presence of at least four HSV US glycoprotein genes (two in VZV), no such homologs were identified.

In application Ser. No. 07/229,011 filed Aug. 5, 1988, including Leland F. Velicer, one of the present inventors, the Marek's Disease herpesvirus DNA encoding the glycoprotein B antigen complex (gp100, gp60, gp49) was identified but not sequenced. Antigen B is an important glycoprotein complex because it can elicit at least partial protective immunity, and the gene can be used for probes, as a possible source for promoters in its 5' regulatory region, and for gene expression to produce the glycoproteins, which in turn can be used to produce antibodies that recognize the glycoprotein antigens. However, there was no discussion of the glycoproteins of the present invention.

In application Ser. No. 07/526,790, filed May 17, 1987 by Leland F. Velicer, the Marek's Disease herpesvirus DNA encoding the glycoprotein A antigen is described but not sequenced. This DNA is useful as probes, as a possible source for promoters in its 5' regulatory region, and for producing antibodies by the sequence of events described above. This DNA is also important because antigen A is now known to be a homolog of HSV gC, a gene non-essential for replication in cell culture. Since that property most likely also applies to the MDV homolog, it may be useful as a site for insertion of foreign genes. However, there was no discussion of the glycoproteins of the present invention.

Little is know about the other glycoproteins produced by Marek's disease herpesvirus. The present invention is directed to the glycoproteins gD, gI and gE.

OBJECTS

It is an object of the present invention to provide sequenced DNA encoding glycoproteins gD, gI and part of gE, both together and individually. It is further an object of the present invention to provide DNA segments encoding these glycoprotein antigens and the up to 400 nucleotides 5' regulatory regions of their genes; which are useful as DNA probes, as a possible source for MDV promoters, for producing antibodies which recognize the antigens and, in the case of the latter two glycoproteins, as likely insertion sites for foreign genes. These and other objects will become increasingly apparent by reference to the following description and the drawings.

IN THE DRAWINGS

FIGS. 1A–C show map location, sequencing strategy and organization of MDV open reading frames (ORFs): A includes MDV genomic structure and restriction maps outlining area sequenced. B includes sequencing strategy. R and L represent rightward- and leftward-directed sequences from M13 clones. The restriction enzyme sites are identified as: B=BamHI, E=EcoRI, N=NcoI, and P=PstI. Sequences derived from random libraries (Sau3A, TaqI, RsaI), specific cloned restriction fragments, Bal31-digested libraries, and using synthetically-derived oligonucleotides are denoted by a, b, c, and d, respectively. C includes organization of nine MDV $U_S$ ORFs. Numbers refer to homologs based on relation to HSV-1 $U_S$ ORF nomenclature (McGeoch, D. J., et al., J. Mol. Biol. 181:1-13. (1985)). SORF1 and SORF2 are MDV-specific S component ORFs given arbitrary names. Upper case and lower case solid bars refer to rightward and leftward-directed ORFs, respectively.

FIGS. 2a through 2h show nucleotide and predicted amino acid sequences. The nucleotide sequence is given as the rightward 5' to 3' strand only (numbered 1 to 8799). Rightward- and leftward-directed predicted amino acid sequences are shown above and below the corresponding nucleotide sequences in single-letter code, respectively. The name of each ORF is given to the left of the first line of the amino acid sequence. Amino acid sequences are numbered from the first M (ATG in the DNA) at the N terminus to the last amino acid at the c-terminus, which precedes the termination codon (identified by a *). Potential TATA consensus sites located within 400 nucleotides of the ATG are underlined and defined as sites containing at least six of seven matches to the TATA(AT)A(AT) consensus sequences defined by Corden et al. (Corden, B., et al., Science 209:1406–1414 (1980)). Underlines longer than seven nucleotides long refer to areas containing overlapping TATA consensus sites.

Figure 3A:
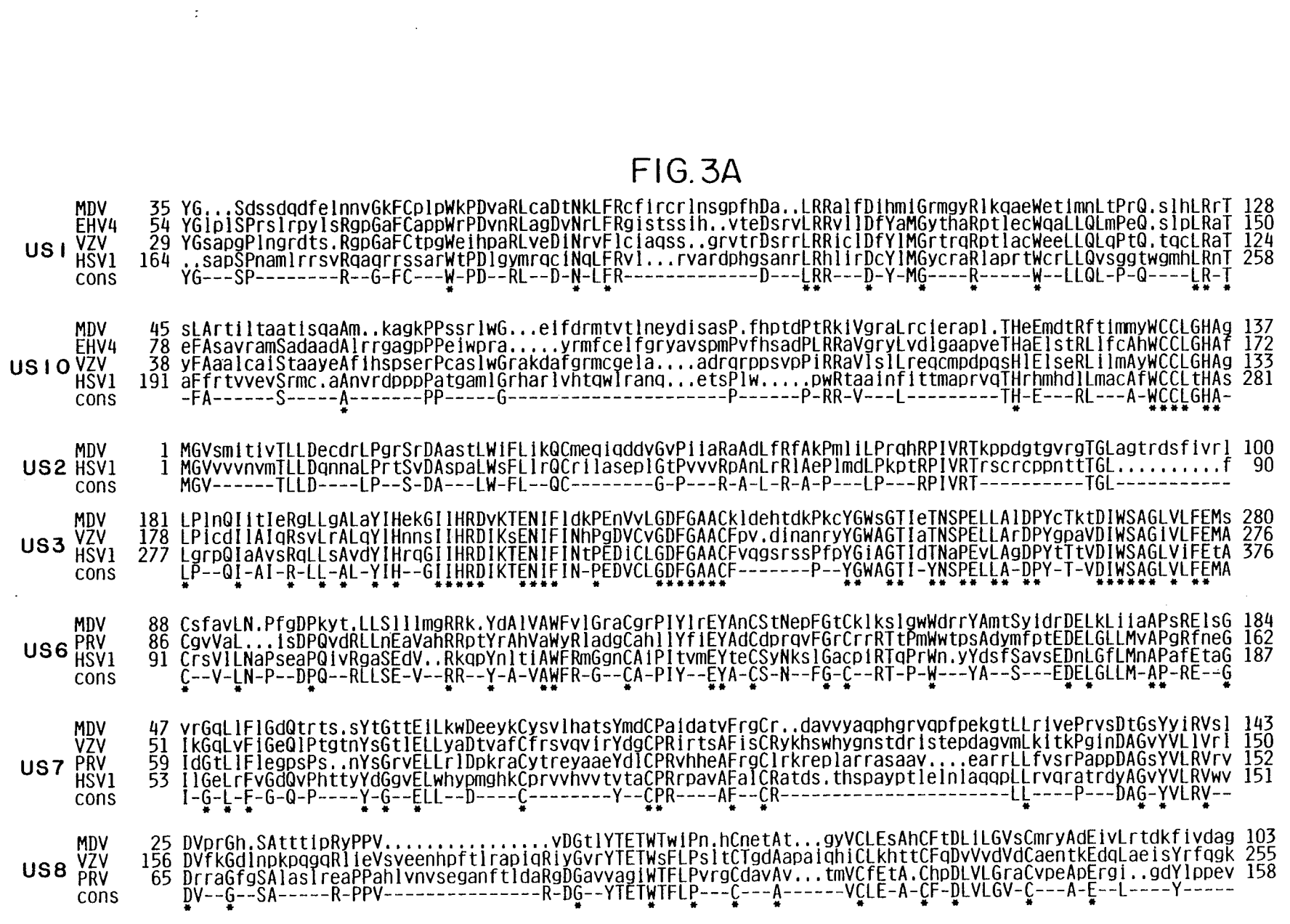

FIG. 3A shows alignment of S component homologs showing selected regions displaying maximum amino acid conservation. Gaps have been introduced to maximize alignment of identical amino acids as described in Methods. The consensus sequence (cons) indicates residues that are shared by at least all but one of the viruses and are indicated by capital letters. In alignments between more than two sequences, asterisks (*) indicate residues conserved by all of the viruses. Amino acid numbers (with respect to 5'-ATG) of corresponding regions aligned are listed before and after each sequence. The HSV-1 US8 homolog was not aligned in order to emphasize the relatedness between the other US8 homologs.

FIG. 3B shows the dot matrix analyses depicting overall homologies between selected MDV-alphaherpesvirus S segment homolog comparisons. Points were generated where at least 15 amino acids over a sliding window length of 30 were found identical or similar. The resulting diagonals illustrate regions showing greatest conservation. Amino acid numbers (with respect to 5'-ATG) of corresponding sequences are denoted above and to the right of each plot.

FIG. 4 shows a comparison of overall genome organization of available S component ORFs (Cullinane, A. A., et al., J. Gen. Virol. 69:1575-1590 (1988); Davison, A. J., et al., J. Gen. Virol. 76:1759-1816 (1986); McGeoch, D. J., et al., J. Mol. Biol. 181:1-13. (1985) Petrovskis, E. A., et al., Virology 159:193-195 (1987); Petrovskis, E. A., et al., J. Virol. 60:185-193 (1986); and Petrovskis, E. A., et al., J. Virol. 59:216-223 (1986)). Numbers above each ORF refer to homologs based on relation to HSV-1 $U_S$ ORF nomenclature (McGeoch, D. J., et al., J. Mol. Biol. 181:1-13. (1985)). Alternative polypeptide designations common to each system are listed below those ORFs where applicable. Upper and lower case solid bars refer to rightward and leftward-directed ORFs, respectively. Arrows refer to identified $IR_S$-$U_S$ and/or $U_S$-$TR_S$ junction sites.

FIG. 5 shows the sequence of steps necessary to produce a complete segment of Marek's disease herpesvirus DNA encoding glycoprotein gI and part of gE.

GENERAL DESCRIPTION

The present invention relates to a segment of DNA of Marek's disease herpesvirus genome encoding multiple glycoproteins, and containing potential promoter sequences up to 400 nucleotides 5' of each gene, between a 1 and 8799 nucleotide sequence as shown in FIG. 2 (and identified as SEQ ID No:1).

Further the present invention relates to an EcoR1 I segment of Marek's disease herpesvirus genome encoding the glycoprotein D precursor, and subsegments of the DNA.

Further still, the present invention relates to a segment of DNA encoding glycoprotein gD precursor between a 5964 and 7175 nucleotide sequence of Marek's disease herpesvirus DNA, and the gene's 5' regulatory region of up to 400 nucleotides in length, as shown in FIG. 2 (and identified as part of SEQ ID No:1) and subsegments of the segment of DNA which recognize the DNA.

The present invention also relates to a segment of DNA encoding glycoprotein gI precursor between a 7282 and 8346 nucleotide sequence of Marek's disease herpesvirus DNA, and the gene's 5' regulatory region of up to 400 nucleotides in length, as shown in FIG. 2 (and identified as part of SEQID No:1) and subsegments of the segments that recognize the DNA.

The present invention also relates to a segment of DNA encoding a part glycoprotein gE precursor between a 8488 and 8799 nucleotide DNA sequence of Marek's disease herpesvirus, and the gene's 5' regulatory region of up to 400 nucleotides in length, as shown in FIG. 1 (and identified as part of SEQ ID No:1) and subfragments of the DNA that recognize the DNA.

Further the present invention relates to the novel glycoprotein precursors which are produced by expression of the genes in the segments of DNA.

Further the present invention relates to the potential MDV gene promoters, which are located in the 400 nucleotides 5' of each coding sequence.

SPECIFIC DESCRIPTION

The present invention shows a sequence analysis of an 8.8 kbp DNA stretch encompassing a majority of the MDV $U_s$ region. Altogether seven MDV $U_s$ homologs, including three glycoprotein genes and two additional MDV-specific open reading frames, were identified.

EXAMPLE 1

Materials and Methods

Recombinant plasmids, M13 subcloning and DNA sequencing MDV EcoR1-0 and EcoR1-I of the pathogenic GA strain were previously cloned into pBR328 by a graduate student at Michigan state University, East Lansing, Mich. (Gibbs, C. P., et al., Proc. Natl. Acad. Sci. USA 81:3365–3369 (1984) and Silva, R. F., et al., J. Virol. 54:690–696 (1985)) and made available by R. F. Silva, USDA Regional Poultry Research Lab, East Lansing, Mich., where these clones are maintained. GA strain BamHI-A and BamHI-P1 were previously cloned into pACYC184 and pBR322, respectively (Fukuchi, K., et al., J. Virol. 51:102–109 (1984)) and kindly provided by M. Nonoyama, Showa University Research Institute, St. Petersburg, Fla. Small- and large-scale plasmid preparations were made using the alkaline lysis procedure (Maniatis, T., et al., Molecular cloning: a laboratory manual. Cold Spring Harbor Laboratory, Cold Spring Harbor, N.Y. (1982)).

M13mp18 and M13mp19 phage subclones to be used as templates for sequencing were generated using specific restriction subfragments determined by restriction mapping or the use of Sau3A, Taq I or RsaI-digested viral DNA pools ligated into the unique BamHI, AccI or SmaI sites of M13 RF DNA, respectively. In some cases overlapping M13 deletion clones were obtained by processive Ba131 digestions from AccI, NaeI or NsiI restriction sites in EcoR1-0 by the method of Poncz et al (Poncz, M., et al., Proc. Natl. Acad. Sci. USA 79:4298–4302 (1982)). Standard methods (Maniatis, T., et al., Molecular cloning: a laboratory manual. Cold Spring Harbor Laboratory, Cold Spring Harbor, N.Y. (1982)) were used for restriction digestions, gel electrophoresis, purification of DNA fragments from agarose gels, ligations and fill-in of 5' overhangs with Klenow fragment.

Ligated M13 products were transformed into $CaCl_2$-competent JM107 host cells and added to melted B top agar containing 10 μl of 100 mM IPTG, 50 μl of 2% X-gal and 200 μl of a fresh overnight JM101 culture. These contents were then plated onto B agar plates and incubated at 37° C. overnight. Recombinant (clear) plaques were then used to infect 5 ml of YT media diluted 1:50 with an overnight JM101 culture and rotated at 37° C. for 6 hours. The resulting cells were pelleted by centrifugation for 5 minutes at room temperature and the supernatants were removed and stored at 4° C. to retain viral stocks of each recombinant clone.

Using the recovered supernatants, single-stranded M13 phage DNA to be used as templates for DNA sequencing by the dideoxy-chain termination method was isolated according to instructions in the M13 Cloning/Dideoxy Sequencing Instruction Manual provided by Bethesda Research Laboratories. Recombinant M13mp phages were further screened by electrophoresing purified single-stranded viral DNA on 1% agarose mini-gels and selecting those templates showing reduced mobility in comparison to single-stranded M13mp 18 control DNA.

DNA sequencing with single-stranded M13 templates was performed by the dideoxy-chain termination method (Sanger, F. s., et al., Proc. Natl. Acad. Sci. USA 74:5463–5467 (1977)) employing the modified T7 DNA polymerase, Sequenase ™ (United States Biochemical Corp., Cleveland, Ohio). A summary of the sequencing strategy is included in FIG. 1B. For DNA sequencing reactions, the specific step by step instructions provided with the Sequenase ™ sequencing kit were employed. Briefly, single-stranded M13 templates were first annealed with the universal M13 synthetic oligonucleotide primer by incubation at 65° C. for 2 minutes followed by slow cooling until the incubation temperature was below 30° C. Following the addition of proper mixtures of deoxy- and dideoxynucleotide triphosphates (dNTPs and ddNTPs, respectively), radioactively labeled deoxyadenosine 5'- (α-thio) triphosphate ($^{35}$S-dATP, 1000–1500 Ci/mmol; NEN-DuPont) and the Sequenase ™ enzyme, synthesis of radioactively labeled complementary strands was initiated from the annealed primer. Four separate synthesis reactions were each terminated by the incorporation of the specific ddNTP (ddATP, ddGTP, ddTTP or ddCTP) used in each tube. Reaction products were electrophorsed through 7% polyacrylamide/50% urea/Tris-Borate-EDTA gels and the labeled chains were visualized by autoradiography. Both strands were sequenced at least once. This was facilitated by the use of 16 synthetic 17-mer oligonucleotides generated based on previously determined sequences and substituted for the universal primer under similar reaction conditions above (0.5 pmoles/reaction) according to the general approach described by Strauss (Strauss, E. C., et al., Anal. Biochem. 154:353–360 (1986)).

Analysis of Sequence Data

Sequences were assembled and analyzed on an IBM personal System 2/Model 50 microcomputer utilizing the IBI/Pustell (Pustell, J., et al., Nucl. Acids. Res. 14:479-488 (1986)) and Genepro (Version 4.10; Riverside Scientific Enterprises, Seattle, Wash.) sequence analysis software packages or programs obtained from the University of Wisconsin Genetics Computer Group (GCG; Devereaux, J., et al., Nucl. Acids. Res. 12:387-395. (1984)) and run on a VAX 8650 minicomputer. Database searches of the National Biochemical Research Foundation-Protein (NBRF-Protein, Release 21.0, 6/89) were made with the GCG program FASTA (Pearson, W. R., et al., Proc. Natl. Acad. Sci. USA 85:2444-2448 (1988)) which uses: (1) a modification of the algorithm of Wilbur and Lipman (Wilbur, W. J., et al., Proc. Natl. Acad. Sci. USA 80:726-730 (1983)) to locate regions of similarity; (2) a PAM250-based scoring system (Dayhoff, M. O., et al., p. 345-352. In M. O. Dayhoff (ed.), Atlas of protein sequence and structure, vol., 5, Suppl. 3. National Biomedical Research Foundation, Washington, D.C. (1978)) and (3) the alignment procedure of Smith and Waterman (Smith, T. F., et al, Adv. Appl. Mathematics 2:482-489 (1981)) to join together, when possible, the highest-scoring, non-overlapping regions in order to derive an alignment and its resulting, optimized score. Dot matrix homology plots were generated by using the GCG program DOTPLOT with the output file from GCG's COMPARE. The latter creates a file of the points of similarity between two predicted amino acid sequences for which a window length of 30 and a stringency of 15 (in which conservative amino acid replacements are scored positive) were chosen. Using the GCG program GAP, specific amino acid sequences were aligned using the algorithm of Needleman and Wunsch (Needleman, S. B., et al., J. Mol. Biol. 48:443-453 (1970)); following the insertion of gaps (to maximize the number of matches) the percentage of identical and similar amino acid residues were determined. To create multiple alignments using GAP, output files of gapped MDV sequences were created following successive GAP comparisons between the MDV sequence and its homologous sequences (in descending order of homology). These output files were used as input sequences for subsequent runs of GAP until the alignment of these gapped sequences could no longer be expanded by the addition of new gaps. Following alignment, the gapped output files were displayed and a consensus sequence calculated using the GCG program PRETTY. To achieve optimal results, in some cases manual editing was employed (using GCG's LINEUP).

Results

The 8,799 nucleotide DNA sequence presented (FIG. 2) appears to encompass a majority of the MDV (GA) genome's unique short (US) region. A summary of the sequencing strategy is included in Materials and Methods and is depicted in FIG. 1B. This sequence spans the US fragments, EcoR1-0, EcoR1-I and extends to the end of BamHI-P$_1$ (FIGS. 1A and B). Fukuchi et al. (Fukuchi, K., et al., J. Virol. 51:102-109 (1984)) have previously mapped the IR$_S$-U$_S$ junction to a 1.4 kb Bgl I fragment located in the second of five EcoR1 subfragments of BamHI-A (FIG. 1B). Thus, the sequence presented here should lack between 2.6 and 4.0 kb of the 5'-proximal U$_S$ region. Because of the lack of available MDV clones mapping downstream of BamHI-P$_1$, the U$_S$-TR$_S$ junction has not yet been precisely defined (Davison, A. J., et al., J. Gen. Virol. 76:1759-1816 (1986)). For VZV, EHV-4 and HSV-1, this border is located about 100 bp upstream or 1.1 and 2.7 kb downstream, respectively, of the termination codon of their respective US8 homologs (Cullinane, A. A., et al., J. Gen. Virol. 69:1575-1590 (1988); Davison, A. J., et al., J. Gen. Virol. 76:1759-1816 (1986); and McGeoch, D. J., et al., J. Gen. Virol. 69:1531-1574 (1988)).

The overall G+C content of the region sequenced was found to be 41%, somewhat below the genomic MDV G+C values of 46% (Lee, L. F., et al., J. Virol. 7:289 (1971)). Observed frequencies of CpG dinucleotides in the whole sequence, or in the coding regions only, did not differ significantly from those expected from their mononucleotide compositions (data not shown). This result agrees with those obtained from alphaherpesviruses, while contrasting with those obtained from gammaherpesviruses, such as the A+T rich HVS and the G+C rich EBV, which are both deficient in CpG dinucleotides (Honess, R. W., et al., J. Gen. Virol. 70:837-855 (1989)).

The region sequenced contains 1 partial and 8 complete ORFs likely to code for proteins (FIG. 1C, basis for names is given below). This prediction was based on: (1) homology and positional organization comparisons to other alphaherpesvirus genes and (2) presence of potential TATA and polyadenylation consensus sequences (Birnstiel, M. L., et al., Cell 41:349-359 (1985); and Corden, B., et al., Science 209:1406-1414 (1980)), and (3) possession of favorable contexts for translational initiation (Kozak, M., J. Cell Biol. 108:229-241 (1989)). This identification was further guided by the observation that alphaherpesviruses such as HSV and VZV tend to contain relatively tightly packed, unspliced and generally nonoverlapping coding regions (Davison, A. J., et al., J. Gen. Virol. 76:1756-1816 (1986); Davison, A. J., et al., J. Gen. Virol. 76:1759-1816 (1986); McGeoch, D. J., et al., J. Gen. Virol. 69:1531-1574 (1988); McGeoch, D. J., et al., J. Mol. Biol. 181:1-13. (1985); and McGeoch, D. J., et al., J. Gen. Virol. 68:19-38 (1987)). Such genes, especially those of the U$_S$ regions, often share polyadenylation signals, thereby resulting in 3'-coterminal mRNA families (Rixon, F. J., et al., Nucl. Acids Res. 13:953-973 (1985)). Methods for detecting protein coding regions based on the use of MDV-derived codon frequency tables (using these and previously published MDV sequences, Binns, M. M., et al., Virus Res. 12:371-382 (1989); Ross, L. J. N., et al., J. Gen. Virol. 70:1789-1804 (1989); and Scott, S. D., et al., J. Gen. Virol. 70:3055-3065 (1989)) or analysis of compositional bias (using the GCG programs CODONPREFERENCE and TESTCODE) were largely inconclusive, suggesting that MDV possesses relatively low codon and compositional biases compared to those predicted based on its mononucleotide composition. However, using the GCG program FRAMES, together with the MDV-derived codon frequency table above, the 9 identified ORFs clearly show a significantly low pattern of rare codon usage, which sharply contrasts with that observed in all other potentially translatable regions (data not shown).

The predicted amino acid sequences of the predicted ORFs (beginning from the first ATG codon) are shown relative to the nucleotide sequence in FIG. 2. Potential TATA sites within 400 nucleotides of the initiation codon are underlined. Proposed ORF and potential polyadenylation signal locations, identification of the −3, +4 ATG context nucleotides (Kozak, M., J. Cell Biol. 108:229-241 (1989)), as well as the lengths, relative molecular masses and predicted isoelectric points of the predicted translational products are shown in Table 1 (set forth at the end of the description). In the absence of previous information concerning these MDV ORFs, and to simplify identification, they have been named (FIG. 1C, Table 1) based on homologous relationships to HSV-1 encoded US ORFs (McGeoch, D. J., et al., J. Mol. Biol. 181:1-13. (1985)). When appropriate, the letters MDV will preface the homolog's name to indicate the ORF's origin. The two MDV-specific ORFs have been arbitrarily named SORF1 and SORF2, based on their location in the S component.

According to the scanning model for translation, the 40s ribosomal subunit binds initially at the 5'-end of mRNA and then migrates, stopping at the first AUG (ATG) codon in a favorable context for initiating translation (Kozak, M., J. Cell Biol. 108:229-241 (1989)). However, in the absence of S1 nuclease and/or primer extension analysis, definitive start sites for translation cannot be accurately predicted. Nevertheless, likely start sites are listed in Table 1; these refer to the location of the first in-frame ATG codon found in the major open reading frame. According to Kozak (Kozak, M., J. Cell Biol. 108:229-241 (1989)), as long as there is a purine in position −3, deviations from the rest of the consensus only marginally impair initiation. In the absence of such a purine, however, a guanine at position +4 is essential for efficient translation. Table 1 shows that all of the ORFs, except for SORF2, contain the important purine residue in the −3 position. Nevertheless, in the case of SORF2, a compensating guanine in position +4 is indeed present.

In the case of MDV US1, two transcriptional cap sites have been tentatively identified by 5' S1 nuclease protection analysis (data not shown). These sites appear to be located 18 and 25 nucleotides downstream of a TATATAA sequence at position 200 and 207, respectively (FIG. 2). Based on 3' S1 data, this transcript utilizes a polyadenylation signal located just downstream of the US10 coding region (Table 1, data not shown). Comparative Northern blot analyses of the US region indicate that the MDV US1 transcript appears to be the most prominent transcript expressed at late times (72h) post-infection when extensive cytopathic effects are observed (data not shown). Phosphonoacetic acid inhibition studies have indicated that MDV US1, in contrast to its immediate-early HSV1 US1 counterpart, is regulated as a late class gene (data not shown).

Using the computer program FASTA (Pearson, W. R., et al., Proc. Natl. Acad. Sci. USA 85:2444-2448 (1988)) with a K-tuple value of 1, each of the 9 predicted amino acid sequences was screened against the NBRF-Protein database (Release 21.0, 6/89), and recently published EHV-4 S segment gene sequences (11). Optimized FASTA scores of greater than 100 were considered to indicate a significant degree of amino acid similarity. The results of this analysis are in Table 2 (set forth at the end of the description). While SORF1 and SORF2 do not appear to share any significant homology to any of the sequences in the database (data not shown), apart from MDV US3, the other six ORFs (MDV US1, 10, 2, 6, 7, and 8; Tables 1, 2) were found to be homologous to alphaherpesvirus S segment genes exclusively (Table 2). Because the US3 ORF represents a member of the serine-threonine protein kinase super-family (Hanks, S. K., et al., science 241:42- (1988)), a relatively large number of scores above 150 were obtained. Nevertheless, these scores were 3-4 fold lower than those obtained in comparisons with Us3 homologs of HSV and VZV. To compare with previously established alphaherpesvirus S segment homologies, all possible FASTA comparisons between the seven groups of alphaherpesvirus-related sequences are included. The program GAP was used in similar pairwise comparisons to generate optimal alignments in order to determine the total percentage of identical and similar amino acids shared by the two sequences. As shown in Table 2, homology comparisons between MDV S segment ORFs and their alphaherpesvirus counterparts were comparable to those previously observed between the other alphaherpesvirus S segment homologs themselves. In some cases MDV ORFs were found to be more related to alphaherpesvirus homologs than those same homologs were to their other alphaherpesvirus counterparts (compare MDV/EHV-4 vs. HSV-1/EHV-4 US1 and MDV/EHV-4 vs. HSV-1/EHV-4 US10 homologies). Moreover, despite the fact that VZV lacks US2 and US6 homologs, MDV, although formally considered a gammaherpesvirus, clearly does possess US2 and US6 homologs. With regard to US8 homologs, pairwise comparisons using GAP were limited to those regions optimally aligned with the partial MDV US8 sequence. Interestingly, the MDV, VZV and PRV US8 homologs exhibit a degree of relatedness over this region that is not shared with HSV-1. The results of limited multiple alignments for each of the seven homologs in which areas showing best conservation are depicted in FIG. 3A.

Dot matrix homology plots depicting overall homologies between selected MDV-alphaherpesvirus s segment homolog comparisons are included in FIG. 3B. (Using a sliding window length of 30 amino acids, in which points are generated where at least 15 amino acids are found identical or similar.) The resulting diagonals illustrate the regions showing greatest conservation. Such regions include and in some cases extend upon those regions depicted in FIG. 3A.

More sensitive attempts to identify other related proteins not detected with FASTA were made using the GCG programs PROFILE and PROFILESEARCH. Use of these programs permit database comparisons which rely on information available from structural studies and, in this case, from information implicit in the alignments of related S component ORFs (including MDV sequences using GAP) (Gribskov, M., et al., Proc. Natl. Acad. Sci. USA 84:4355-4358 (1987)); nevertheless, such analyses failed to extend upon the groups of related proteins described here.

Herpesvirus glycoprotein homologs have generally been found to contain similar patterns of conserved cysteine residues. In comparing the gB homologs of seven different herpesviruses included in the alpha-, beta- and gammaherpesvirus subclasses, there is complete conservation of 10 cysteine residues (Ross, L. J. N., et al., J. Gen. Virol. 70:1789-1804 (1989)). HSV-1 US6(gD) contains 7 cysteine residues: six appear critical for correct folding, antigenic structure and extent of oligosaccharide processing (Wilcox, W. C., et al., J. Virol. 62:1941-1947 (1988)). Not only is this same general pattern of cysteines conserved in the gD homologs of HSV-2 (McGeoch, D. J., et al., J. Gen. Virol. 68:19-38 (1987)) and PRV (Petrovskis, E. A., et al., J. Virol. 59:216-223 (1986)), but they are conserved in the MDV gD homolog as well (full alignment not shown). FIG. 3A depicts portions of cysteine conservation patterns observed among the US6 (gD), US7 (gI), and US8 (gE) homologs (in which case 4, 3, and 4 conserved cysteine residues are shown, respectively). Interestingly, the basis for the relatively high degree of homology between gE homologs of MDV, VZV and PRV over the limited area described above is largely based on a unique, shared pattern of relatively rare cysteine residues which HSV-1 lacks. While the HSV-1, VZV and PRV gE homologs (and probably MDVs) are known to share six different cysteines located further downstream, it is quite possible that the unique pattern of four conserved cysteines could facilitate the formation of different secondary and tertiary structures which might impart important functional consequences.

Careful inspection of the N-terminal regions of the MDV gD, gI and gE homologs has revealed that they contain the three basic building blocks of signal peptide sequences: a basic, positively charged N-terminal region (n-region), a central hydrophobic region (h-region), and a more polar terminal region (c-region) that seems to define the cleavage site (von Heijne, G. J. Mol. Biol. 184:99–105 (1985)). Using a recently improved method for predicting signal sequence cleavage sites (von Heijne, G. Nucl. Acids Res. 14:4683–4690 (1986)), Table 3 (set forth at the end of the description) shows the likely position of these sites, the location of the hydrophobic transmembrane and charged cytoplasmic domains near the C-terminal end and the location of potential N-glycosylation sites. Like the other gI homologs, MDV's counterpart contains a relatively long cytoplasmic domain. However, in contrast to the other gD homologs, MDV gD's signal peptide contains a relatively long n-region (18 residues), that is unusually highly charged (+4; FIG. 2) considering an overall mean value of +1.7 among eukaryotes, which generally does not vary with length (von Heijne, G. J. Mol. Biol. 184:99–105 (1985)). Although a more distal methionine codon exists directly before the hydrophobic initiator codon (as in the PRV gD homolog, Petrovskis, E. A., et al., J. Virol. 59:216–223 (1986)) the scanning model for translation (Gribskov, M., et al., Proc. Natl. Acad. Sci. USA 84:4355–4358 (1987)) favors usage of the more 5'-proximal initiation codon (at position 5964, FIG. 2). Further support is based on an overall translation context that appears at least as good, if not better than the one corresponding to the downstream ATG. Despite such a prediction, a possible mRNA cap site location between the two ATG sites, which would preclude such a prediction, cannot be ruled out at this point.

One final point concerning MDV gD requires mention. Using the 8,799 nucleotide DNA sequence as a probe for screening the GenBank (62.0, 12/89) and EMBL (19.0, 5/89) nucleic acid databases with the computer program FASTA (K-tuple=6), an optimized score of 1027, corresponding to 91.5% nucleotide identity in a 342 bp overlap between MDV gD coding sequences (6479-6814; aa#173-aa#284; FIG. 2) and a previously reported 467 bp MDV DNA segment (Wen, L.-T., et al., J. Virol. 62:3764-3771 (1988)). The latter sequence has been reported to contain a 60 bp segment protected against DNAase digestion by binding of a 28 kD MDV nuclear antigen (MDNA) expressed only in "latently" infected MDV-transformed lymphoblastoid cells. In view of similarities between MDV and VZV, these authors suggested that MDNA may function in a manner analogous to that of EBNA-1 in immortalizing primate cells. In their report, Wen et al. (Wen, L.-T., et al., J. Virol. 62:3764-3771 (1988)) mapped the MDNA binding site to the same EcoRI subfragment of BamHI-A in which MDV gD is located (EcoRI-I, FIG. 1) Although our sequence covering this region is consistent with a complete, uninterrupted ORF containing all the characteristic features of a glycoprotein and showing significant homology to HSV gD, their sequence contains about 140 bases of 5'-proximal sequence unrelated to any determined from our 5.3 kbp EcoR1-I fragment or its adjoining 3.5 kb sequences. The remaining 327 bp sequence (which contains the putative nuclear antigen binding site) while clearly resembling our gD coding sequence, upon computer translation fails to yield any ORF longer than 30 aa.

Discussion

Recent data have shown that despite MDV's classification as a gammaherpesvirus, based on lymphotropic properties shared with other members of this subfamily, its genome structure (Cebrian, J., et al., Proc. Natl. Acad. Sci. USA 79:555–558 (1982); and Fukuchi, K., et al., J. Virol. 51:102–109 (1984)) and genetic organization of primarily its $U_L$ region (Buckmaster, A. E., et al., J. Gen. Virol. 69:2033–2042 (1988)) more closely resembles that of the neurotropic alphaherpesviruses. Moreover, in cases where polypeptide sequences were found conserved among the three herpesvirus subfamilies (e.g. $U_L$ genes), significantly higher homology scores were consistently observed against the respective alpha- rather than beta- or gammaherpesvirus counterparts (Davison, A. J., et al., J. Gen. Virol. 67:597–611 (1986); Buckmaster, A. E., et al., J. Gen. Virol. 69:2033–2042 (1988); Ross, L. J. N., et al., J. Gen. Virol. 70:1789–1804 (1989); and Scott, S. D., et al., J. Gen. Virol. 70:3055–3065 (1989)). Alphaherpesvirus S segment genes have previously been found to be unique to members of this taxonomic subfamily (Davison, A. J., et al., J. Gen. Virol. 68:1067–1079 (1987); and Davison, A. J., et al., J. Gen. Virol. 67:597–611 (1986). The identification of seven MDV homologs of alphaherpesvirus S segment genes in this study is consistent with the idea that MDV shares a closer evolutionary relationship with alphaherpesviruses than gammaherpesviruses. This is further supported by dinucleotide frequency analysis which fails to show a lack of CpG suppression as observed among all gammaherpesviruses thus far studied (Efstathiou, S., et al., J. Gen. Virol. 71:1365–1372 (1990); and Honess, R. W., et al., J. Gen. Virol. 70:837–855 (1989)). The above situation resembles a similar one observed with human herpesvirus-6 (HHV-6), in which case its T-lymphotropism suggested provisional classification as a gammaherpesvirus (Lopez, C., et al., J. Infect. Dis. 157:1271–1273 (1988)). However, subsequent genetic analysis has shown a greater relatedness between HHV-6 and the betaherpesvirus, human cytomegalovirus (HCMV; Lawrence, G. L., et al., J. Virol. 64:287–299 (1990)).

A comparison of the genetic organization of alphaherpesvirus S segment genes in presented in FIG. 4. The organization of these genes differ greatly in overall length, organization and degree of homology. Nevertheless, the overall gene layouts displayed are consistent with a model to account for the divergence of alphaherpesviruses from a common ancestor by a number of homologous recombination events which result in expansion or contraction of the inverted repeat regions and a concomitant loss or gain of $U_s$ gene(s). In the case of VZV, six S segment homologs are lacking compared to HSV-1 (US2, US4, US5, US6, US11, US12). Some genes, such as the US1 homologs, show particular sequence and length divergences. Compared to HSV-1, the MDV, VZV and EHV-4 US1 homologs lack approximately 120 aa of sequence comparable to the 5'-proximal portion of HSV-1 US1 (α22). Based on Northern blot analysis, S1 nuclease protection analysis and phosphonoacetic acid inhibition studies, in contrast to its relatively uncharacterized immediate-early HSV-1 counterpart, the MDV US1 gene appears to be regulated as an abundantly expressed late class gene (data not shown). In contrast to the other alphaherpesviruses, MDV contains two apparently MDV-specific ORFs. Moreover, the MDV $U_S$ region appears to contain approximately 2.6 to 4.0 kb of additional 5'-proximal sequences. Based on a comparison of FIG. 4 and consideration of the expansion-contraction recombination scheme, it appears likely that there are additional MDV-specific $U_S$ genes.

Since MDV has long been regarded as a gammaherpesvirus, much of the previous work interpreting their properties has proceeded by analogy with the association between EBV and B cells (Nonoyama, M. p. 333–341. In B. Roizman (ed.), The herpesviruses, vol. 1 Plenum Press (1982); and Wilbur, W. J., et al., Proc. Natl. Acad. Sci. USA 80:726–730 (1983)). Because of a closer genetic relationship to the alphaherpesviruses, and keeping in mind the analysis of HHV-6 above we agree with Lawrence et al. (Lawrence, G. L., et al., J. Virol. 64:287–299 (1990)) that the lymphotropic properties of MDV and HVT are unlikely to be determined by molecules homologous to EBV and that a delineation of molecular differences between MDV and the neurotropic alphaherpesviruses would be more fruitful in explaining the observed biological differences than employing analogies based on properties of gammaherpesviruses such as EBV and HVS.

To account for such differences, the MDV $U_S$ region may be particularly important. With few exceptions, each HSV-1 L component gene possesses an equivalent in VZV (McGeoch, D. J., et al., J. Gen. Virol. 69:1531–1574 (1988)); a considerable number of these are related to beta- and gammaherpesvirus genes as well (29 of 67 EBV counterparts to VZV $U_L$ genes; Davison, A. J., et al., J. Gen. Virol. 68:1067–1079 (1987)). In contrast, the S segments of HSV-1 and VZV differ significantly in size and appear to be among the least related parts of the two genomes (Davison, A. J., et al., J. Gen. Virol. 67:597–611 (1986; and Davison, A. J., et al., J. Gen. Virol. 64:1927–1942 (1983)). Recent studies have shown that 11 of 12 open reading frames contained in the HSV-1 S component are dispansable for growth in cell culture (Longnecker, R., et al., Proc. Natl. Acad. Sci. USA 84:4303–4307 (1987); and Weber, P. C., et al., Science 236:576–579 (1987)). The maintenance and evolution of such a dispensable gene cluster suggests the presence of functions relevant to the viruses survival in its specific ecological niche in the natural or laboratory animal host, rather than the presence of functions necessary for replication (Longnecker, R., et al., Proc. Natl. Acad. Sci. USA 84:4303–4307 (1987); and Weber, P. C., et al., Science 236:576–579 (1987)). Consistent with such a hypothesis are findings that HSV mutants carrying different S component gene-specific deletions were significantly less pathogenic and exhibited a reduced capacity for latency establishment in mice (Meignier, B., et al., Virology 162:251–254 (1988)). In regard to the latter, there is evidence suggesting that transcribed RNA from the HSV $U_S$ region may be involved in the establishment and maintenance of an in vitro latency system employing human fetus lung fibroblast cells (Scheck, A. C., et al., Intervirology 30:121–136 (1989)). Taken together, the above evidence suggest(s) potentially important role(s) for MDV's $U_S$ genes in tissue tropism, latency, and/or induction of cell transformation.

A consideration of the three gD, gI and gE homologs identified in this invention raises an interesting question. Fully enveloped infectious MDV virions are only known to be produced in feather follicle epithelial cells (Payne, L. N. p. 347–431. In B. Roizman (ed.), The herpesviruses, vol. 1. Plenum Press (1982)). Because of this, MDV studies have had to rely on limited fibroblast cell cultures which only promote the spread of cell-associated infections in vitro. Over the last 20 years, studies aimed at identifying immunogenic surface antigens have relied on this in vitro culture system and altogether only two glycoprotein antigens (A antigen/gC homolog; B antigen) have been routinely identified and characterized (Binns, M. M., et al., Virus Res. 12:371–382 (1989); Coussens, P. M., et al., J. Virol. 62:2373–2379 (1988); Isfort, R. J., et al., J. Virol. 59:411–419 (1986); Isfort, R. J., et al., J. Virol. 57:464–474 (1986); and sithole, I., et al., J. Virol. 62:4270–4279 (1988)). This is despite findings of three MDV gD, gI and gE homologs of the present invention and two additional glycoprotein homologs (gB and gH; Buckmaster, A. E., et al., J. Gen. Virol. 69:2033–2042 (1988); and Ross, L. J. N., et al., J. Gen. Virol. 70:1789–1804 (1989)). While immune chicken sera (ICS) from naturally infected birds is likely to react with many, if not all, MDV-encoded surface antigens, this complex polyclonal sera would only be useful to the extent that antigen expression/processing in semi-productive cell cultures resembles that in feather follicle epithelial cells. Northern blot analysis using MDV gD-specific probes suggests that MDV gD mRNA is either not expressed or poorly expressed in DEF cells at a time when extensive cytopathic effects are observed (data not shown). In light of the fact that VZV lacks a gD homolog and is strongly cell-associated, it will be interesting to see whether the block in MDV virion formation in primary avian fibroblast cells is found to correlate with lack of expression (in these cells) of a glycoprotein, such as gD, and/or some other S component gene(s).

Because the protection against MD conferred by attenuated MDV strains (serotype 2) or HVT (serotype 3) appears to have an immunological basis, there is considerable interest in identifying common antigens. In view of this invention identifying seven MDV $U_S$ homologs to $U_S$ genes of HSV (the latter of which is clearly less related to MDV than HVT is), it would be surprising if the previous report showing lack of homology between MDV-HVT $U_S$ regions (Igarashi, T., et al., Virology 157:351–358 (1987)) were proven correct. Such negative results may reflect the limitations regarding homology estimates based on hybridization, rather than sequence analysis studies.

Example 2 shows the molecular cloning of a construct containing the DNA encoding the complete MDV US7 (gI) and part of MDV US8 (gE) genes. As can be seen, this is accomplished using segments of DNA spanning the gI and part of the gE coding region.

EXAMPLE 2

Molecular Cloning of a Construct Containing the DNA Encoding the Complete MDV US7 (gI) and Part of MDV US8 (gE)

Construction of a recombinant clone (pKS-MDgI1.59) containing the complete MDV US7 (gI) coding sequence and a portion of the MDV US8 (gE) coding sequence requires two preexisting MDV clones, pKS-MDgD1.75 and p19P1 (FIG. 5). pKS-MDgD1.75 is a recombinant plasmid containing the 1.75 kbp NcoI-SstII subfragment of MDV EcoR1-I ligated into the SmaI-Sst II site of the cloning vector, pBluescript KS-. This clone contains the complete MDV US6 (gD) coding sequence and additional sequences at the 3′ end which code for the first 39 amino acids (aa) of MDV gI. p19P1 is a recombinant plasmid containing the 1.5 kbp BamHI-P₁ subfragment of MDV cloned into the unique BamHI site of pUC19. This clone contains the entire MDV gI coding sequence, except for the first 9 as of its signal sequence. In addition, at the 3′ end, p19P1 contains the first 104 aa of the MDV US8 (gE) coding region.

To generate pKS-MDgI1.59, pKS-MgD1.75 is first cut with Hinc II, which cuts once in the multiple cloning site of the pBluescript vector and once about 180 bp upstream of the insert's Sst II terminus. This results in two fragments: one fragment (1.6 kbp) consists primarily of insert sequences encoding MDV US6(gD); the larger fragment (3.1 kbp) consists of pBluescript vector sequences, in addition to about 180 bp which encode the N-terminus of MDV gI. The 3.1 kb fragment is gel purified and self-ligated by way of the two Hinc II ends. The resulting recombinant plasmid, pKS-MDgI0.18, is then cut with Sst I (in the multiple cloning site, just downstream of the Sst II site). Prior to subsequent digestion with SstII, the cohesive Sst I ends is made blunt-ended with T4 DNA polymerase. The resulting 3.1 kbp Sst II-Set I(blunt) fragment of pMDgI0.18 is gel purified and used in the final ligation step to create pKS-MDgI1.59. While the enzymatic manipulations of pKS-MgD1.75 and pKS-MDgI0.18 are taking place, p19P1 is cut with Hind III, which cuts just downstream of the partial MDV US8 (gE) coding sequence in the multiple cloning site of pUC19. Prior to digestion with SstII, the cohesive Hind III ends is made blunt-ended using Klenow fragment. The smaller Sst II-Hind III(blunt) fragment (1.4 kbp) contains a majority of the MDV US7 (gI) coding sequence, in addition to 312 nucleotides at the 3′ end which code for the 5′ end of MDV gE. This 1.4 kbp Sst II-Hind III(blunt) fragment is gel purified and ligated to the 3.1 kbp Sst II-Sst I(blunt) fragment of pKS-MDgD0.18. The resulting recombinant, pKS-MDgI1.59, contains the complete coding sequence for MDV gI and a portion of the N-terminal gE coding sequence. Digestion of pKS-MDgI1.59 with KpnI yields two fragments; the smaller 1.15 kbp fragment contains the complete coding sequence for MDV gI.

Plasmid pKS-MDgI1.59, containing the DNA sequences encoding the complete glycoprotein MDV gI and part of the glycoprotein MDV gE, is on deposit at Michigan State University.

Example 3 shows the strategy for isolating a construct containing complete MDV US8 gene. As can be seen, this is accomplished by using a segment of DNA encoding the N terminal end of the gE gene as a radiolabeled probe to screen genomic and/or cDNA libraries.

EXAMPLE 3

Strategy for Isolating a Construct Containing Complete MDV US8 (gE) Gene

Double digestion of pKD-MDgI1.59 with KpnI and BamHI yields a 425 bp KpnI-BamHI subfragment containing the coding sequences for the N-terminal 104 amino acids of MDV gE. This subfragment is radiolabelled and used as a probe to screen both genomic and cDNA libraries of MDV in order to locate clones containing the complete MDV gE gene. Positively hybridizing clones are further characterized and sequenced in order to better define the complete structure of this gene.

A summary of MDV data is shown in Table 1, with location of ORFs, predicted polyadenylation signals utilized, translational context nucleotides, lengths, relative molecular sized and isoelectric points of predicted translation products.

TABLE 1

| Name | ORF Start | ORF End | Predicted Polyadenylation Site | −3, +4 ATG[a] Context Nucleotides | Length(aa) | Predicted Molecular Size(kDa) | Predicted pI[b] |
|---|---|---|---|---|---|---|---|
| US1 | 248 | 784 | 1777 | A,A | 179 | 20.4 | 6.5 |
| US10 | 1077 | 1715 | 1777 | G,G | 213 | 23.6 | 8.2 |
| SORF1 | 2884 | 1832 | 1790 | A,A | 351 | 40.6 | 8.2 |
| US2 | 3923 | 3114 | 1790 | A,G | 270 | 29.7 | 7.6 |
| US3 | 4062 | 5240 | 5394 | A,G | 393 | 43.8 | 6.1 |
| SORF2 | 5353 | 5793 | 5904 | C,G | 147 | 16.7 | 9.8 |
| US6 | 5964 | 7172 | c | G,G | 403 | 42.6[d] | 10.3[d] |
| US7 | 7282 | 8346 | c | G,T | 355 | 38.3[d] | 6.7[d] |
| US8 | 8488 | e | c | A,T | e | e | e |

[a]Nucleotides listed relative to −3, +4 positions, respectively; numbering begins with the A of the ATG (AUG) codon as position +1; nucleotides 5′ to that site are assigned negative numbers.
[b]Calculated using the GCG program, ISOELECTRIC.
[c]Likely to use undefined site just downstream of US8 termination condon.
[d]Based on sequences that follow the predicted signal peptide cleavage site.
[e]Incomplete ORF.

Table 2 shows FASTA scores[a] and similarity/identity percentages[b] obtained from pairwise homology comparisons between respective predicted amino acid sequences.

TABLE 2

| Virus | US1 | | | | US10 | | | | US2 | | US3 | | |
|---|---|---|---|---|---|---|---|---|---|---|---|---|---|
| | MDV | HSV-1 | VZV | EHV-4 | MDV | HSV-1 | VZV | EHV-4 | MDV | HSV-1 | MDV | HSV-1 | VZV |

TABLE 2-continued

| | | | | | | | | | | | | | | |
|---|---|---|---|---|---|---|---|---|---|---|---|---|---|---|
| MDV | 891 | 47/26 | 43/27 | 48/30 | 1071 | 45/24 | 40/24 | 45/29 | 1421 | 51/33 | 1931 | 56/38 | 54/33 |
| HSV-1 | 101 | 2047 | 49/29 | 50/29 | 134 | 1617 | 49/27 | 49/27 | 335 | 1554 | 611 | 2409 | 57/41 |
| VZV | 160 | 119 | 1378 | 54/36 | 147 | 123 | 978 | 55/32 | — | — | 616 | 717 | 1960 |
| EHV-4 | 208 | 150 | 359 | 1308 | 251 | 180 | 191 | 1312 | | | | | |
| PRV | | | | | | | | | ? | ? | ? | ? | ? |
| Length (aa) | 179 | 420 | 278 | 273 | 213 | 312 | 180 | 259 | 270 | 291 | 393 | 481 | 393 |

| | US6 | | | US7 | | | | US8* | | | |
|---|---|---|---|---|---|---|---|---|---|---|---|
| Virus | MDV | HSV-1 | PRV | MDV | HSV-1 | VZV | PRV | MDV | HSV-1 | VZV | PRV |
| MDV | 1965 | 43/22 | 44/24 | 1816 | 39/22 | 46/23 | 43/25 | 538 | 36/17 | 44/29 | 47/30 |
| HSV-1 | 211 | 1999 | 47/27 | 145 | 1880 | 43/24 | 47/25 | 56 | 583 | 40/19 | 44/23 |
| VZV | — | — | — | 228 | 234 | 1705 | 41/26 | 109 | 30 | 624 | 47/30 |
| EHV-4 | | | | 184 | 188 | 198 | 1652 | 103 | 59 | 103 | 593 |
| PRV | 279 | 294 | 2116 | | | | | | | | |
| Length (aa) | 403 | 394 | 402 | 355 | 390 | 354 | 350 | 104 | 118 | 126 | 125 |

[a] FASTA scores represented by single numbers in lower left of boxes.
[b] Similarity/identity percentages are derived from pairwise GAP comparisons and are located in upper right of boxes.
— no VZV homolog.
? PRV homologs identified (M. M. van Zijl, J. M. L. vander Gulden, A. L. J. Gielkens and A. J. M. Berns. Abstr. 14th Int. Herpesvirus Workshop, p. 5, 1989), but published sequences not available
*regions compared limited to those aligned with the partial MDV US8 sequence Table 3 shows MDV $U_S$ glycoprotein data on predicted signal peptide cleavage sites and locations of transmembrane and cytoplasmic domains and potential N-glycosylation sites (with respect to initiator ATG codon)

TABLE 3

| Name | Predicted Signal Peptide Cleavage Site | Trans-membrane Domain | Cyto-plasmic Domain | N-glycosylation Sites |
|---|---|---|---|---|
| US6 | $G_{30}$-$D_{31}$ | 358–374 | 375–403 | 87, 138, 230, 306 |
| US7 | $S_{18}$-$I_{19}$ | 269–288 | 289–355 | 147, 167, 210, 245, 253, 317 |
| US8 | $T_{18}$-$A_{19}$ | a | a | a |

[a] incomplete ORF

Index of definition of letters in FIG. 2. Table 4 showing the amino acids with both their single letter and three letter symbols.

TABLE 4

| A | Ala | Alanine | M | Met | Methionine |
|---|---|---|---|---|---|
| C | Cys | Cysteine | N | Asn | Asparagine |
| D | Asp | Aspartic Acid | P | Pro | Proline |
| E | Glu | Glutamic Acid | Q | Gln | Glutamine |
| F | Phe | Phenylalanine | R | Arg | Arginine |
| G | Gly | Glycine | S | Ser | Serine |
| H | His | Histidine | T | Thr | Threonine |
| I | Ile | Isoleucine | V | Val | Valine |
| K | Lys | Lysine | W | Trp | Tryptophan |
| L | Leu | Leucine | Y | Tyr | Tyrosine |

ATCC Deposit

The gene for MDV US6 (MDV gD) has been deposited in a plasmid (phagemid) PKS-MDgD1.75, as ATCC 40855, with The American Type Culture Collection, Rockville, Md., 20852, U.S.A.

We claim:

1. The substantially pure glycoprotein gE precursor which comprises:

Met Cys Val Phe Gln Ile Leu Ile Ile Val Thr Thr Ile Lys Val Ala
−15                    −10                    −5

Gly Thr Ala Asn Ile Asn His Ile Asp Val Pro
1                5

Arg Gly His Ser Ala
10

Thr Thr Thr Ile Pro Arg Tyr Pro Pro Val
15                20

Val Asp Gly Thr Leu Tyr
25                30

Thr Glu Thr Trp Thr Trp Ile Pro Asn
35

His Cys Asn Glu Thr Ala Thr
40                45

Gly Tyr Val Cys Leu Glu Ser Ala
50

His Cys Phe Thr Asp Leu Ile Leu
55                60

Gly Val Ser Cys Met Arg Tyr
65

Ala Asp Glu Ile Val Leu Arg Thr Asp
70                75

Lys Phe Ile Val Asp Ala Gly Ser.
80                85

* * * * *

UNITED STATES PATENT AND TRADEMARK OFFICE
CERTIFICATE OF CORRECTION

PATENT NO. : 5,138,033
DATED : August 11, 1992
INVENTOR(S) : Leland F. Velicer, Peter Brunovskis and Paul M. Coussens It is certified that error appears in the above-identified patent and that said Letters Patent is hereby corrected as shown below:

Title Page, Abstract, "glycopropteins" should be --glycoproteins--

Column 3, line 27, "know" should be --known--.

Column 6, line 35, "(Sanger, F. s., et al" should read --(Sanger, F. S., et al--.

Column 6, line 57, "electrophorsed" should be --electrophoresed--.

Column 5, line 44, "Michigan state University" should read --Michigan State University--.

Column 10, line 1, "science" should be --Science--.

Column 12, line 60 "genes in" should read --genes is--.

Column 14, line 28, "sithole" should be --Sithole--.

Column 15, line 20, "9 as" should read --9 aa--.

UNITED STATES PATENT AND TRADEMARK OFFICE
CERTIFICATE OF CORRECTION

PATENT NO. : 5,138,033
DATED : August 11, 1992
INVENTOR(S) : Leland F. Velicer, Peter Brunovskis and Paul M. Coussens It is certified that error appears in the above—identified patent and that said Letters Patent is hereby corrected as shown below:

Column 15, line 39, "Sst II- Set I" should read --Sst II - Sst I--.

Column 15, line 62, "MgD1.75" should read --MDgD1.75--.

Column 16, line 19, "US8 gene" should read --US8 (gE) gene--.

Column 16, line 28, "pKD-MDgI 1.59" should read --pKS-MDgI 1.59--.

Column 16, under footnote c of Table, "condon" should be --codon--.

Signed and Sealed this

Thirty-first Day of May, 1994

Attest:

BRUCE LEHMAN

Attesting Officer    Commissioner of Patents and Trademarks